US012697178B2

(12) United States Patent　　　　　(10) Patent No.:　US 12,697,178 B2
Oberkircher　　　　　　　　　　　　(45) Date of Patent:　Aug. 4, 2026

(54) SURGICAL FOOTSWITCH ASSIGNMENT FOR MODULAR ENERGY SYSTEM

(71) Applicant: Cilag GmbH International, Zug (CH)

(72) Inventor: Brendan J. Oberkircher, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 947 days.

(21) Appl. No.: 17/851,687

(22) Filed: Jun. 28, 2022

(65) Prior Publication Data

US 2023/0414298 A1　　Dec. 28, 2023

(51) Int. Cl.
| | |
|---|---|
| *A61B 34/00* | (2016.01) |
| *A61B 18/00* | (2006.01) |
| *G06F 3/023* | (2006.01) |
| *G06F 3/0486* | (2013.01) |
| *G06F 9/451* | (2018.01) |
| *A61B 17/00* | (2006.01) |

(52) U.S. Cl.
CPC .............. *A61B 34/25* (2016.02); *G06F 3/023* (2013.01); *G06F 3/0486* (2013.01); *G06F 9/453* (2018.02); *A61B 2017/00973* (2013.01)

(58) Field of Classification Search
CPC ...... A61B 34/25; A61B 2034/252–258; A61B 2017/00973; G06F 9/453; G06F 3/023; G06F 3/0486
See application file for complete search history.

(56) References Cited

U.S. PATENT DOCUMENTS

| | | | |
|---|---|---|---|
| 4,171,700 | A | 10/1979 | Farin |
| 4,378,801 | A | 4/1983 | Oosten |
| 4,640,279 | A | 2/1987 | Beard |

(Continued)

FOREIGN PATENT DOCUMENTS

| | | |
|---|---|---|
| EP | 0408160 A1 | 1/1991 |
| EP | 0473987 A1 | 3/1992 |

(Continued)

OTHER PUBLICATIONS

Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.

(Continued)

*Primary Examiner* — Adam Z Minchella
(74) *Attorney, Agent, or Firm* — FBT Gibbons LLP

(57)　　　　ABSTRACT

Devices, systems, and methods for assigning footswitches to control specific ports of modular energy systems are disclosed herein. In some aspects, a modular energy system can include an energy module and a display screen. The energy module can include a plurality of ports. The display screen can be configured to render a graphical user interface (GUI). The GUI can be configured to display a plurality of widgets corresponding to the ports and display an object indicating that a footswitch is available to be assigned to one of the ports. The GUI can be further configured to allow a user to drag and drop the object into one of the widgets. Dragging and dropping the object into one of the widgets can cause the modular energy system to assign the footswitch to the port corresponding to the widget.

17 Claims, 18 Drawing Sheets

(56) References Cited

U.S. PATENT DOCUMENTS

| | | | |
|---|---|---|---|
| 4,849,752 | A | 7/1989 | Bryant |
| D303,787 | S | 10/1989 | Messenger et al. |
| 5,041,110 | A | 8/1991 | Fleenor |
| D327,061 | S | 6/1992 | Soren et al. |
| 5,189,277 | A | 2/1993 | Boisvert et al. |
| 5,204,669 | A | 4/1993 | Dorfe et al. |
| 5,318,563 | A | 6/1994 | Malis et al. |
| 5,325,270 | A | 6/1994 | Wenger et al. |
| 5,425,375 | A | 6/1995 | Chin et al. |
| D379,346 | S | 5/1997 | Mieki |
| 5,690,504 | A | 11/1997 | Scanlan et al. |
| 5,693,042 | A | 12/1997 | Boiarski et al. |
| 5,724,468 | A | 3/1998 | Leone et al. |
| 5,788,688 | A | 8/1998 | Bauer et al. |
| 5,910,139 | A | 6/1999 | Cochran et al. |
| 6,049,467 | A | 4/2000 | Tamarkin et al. |
| 6,055,458 | A | 4/2000 | Cochran et al. |
| D431,811 | S | 10/2000 | Nishio et al. |
| 6,179,136 | B1 | 1/2001 | Kluge et al. |
| 6,269,411 | B1 | 7/2001 | Reasoner |
| 6,273,750 | B1 | 8/2001 | Malkowski, Jr. |
| 6,288,606 | B1 | 9/2001 | Ekman et al. |
| 6,416,471 | B1 | 7/2002 | Kumar et al. |
| 6,546,270 | B1 | 4/2003 | Goldin et al. |
| 6,584,358 | B2 | 6/2003 | Carter et al. |
| 6,611,793 | B1 | 8/2003 | Burnside et al. |
| 6,731,514 | B2 | 5/2004 | Evans |
| 6,760,218 | B2 | 7/2004 | Fan |
| 6,839,238 | B2 | 1/2005 | Derr et al. |
| 6,843,657 | B2 | 1/2005 | Driscoll et al. |
| 6,913,471 | B2 | 7/2005 | Smith |
| 7,009,511 | B2 | 3/2006 | Mazar et al. |
| 7,044,949 | B2 | 5/2006 | Orszulak et al. |
| 7,074,205 | B1 | 7/2006 | Duffy et al. |
| 7,134,994 | B2 | 11/2006 | Alpert et al. |
| 7,171,784 | B2 | 2/2007 | Eenigenburg |
| 7,217,269 | B2 | 5/2007 | El-Galley et al. |
| 7,252,664 | B2 | 8/2007 | Nasab et al. |
| D562,342 | S | 2/2008 | Cameron |
| 7,331,699 | B2 | 2/2008 | Gawalkiewicz et al. |
| 7,344,532 | B2 | 3/2008 | Goble et al. |
| D565,587 | S | 4/2008 | Sadler et al. |
| 7,353,068 | B2 | 4/2008 | Tanaka et al. |
| D575,792 | S | 8/2008 | Benson |
| 7,408,439 | B2 | 8/2008 | Wang et al. |
| D579,876 | S | 11/2008 | Novotney et al. |
| D583,328 | S | 12/2008 | Chiang |
| 7,496,418 | B2 | 2/2009 | Kim et al. |
| D589,447 | S | 3/2009 | Sasada et al. |
| 7,500,747 | B2 | 3/2009 | Howell et al. |
| 7,518,502 | B2 | 4/2009 | Austin et al. |
| 7,563,259 | B2 | 7/2009 | Takahashi |
| 7,601,149 | B2 | 10/2009 | DiCarlo et al. |
| 7,637,907 | B2 | 12/2009 | Blaha |
| 7,656,671 | B2 | 2/2010 | Liu et al. |
| D616,895 | S | 6/2010 | Ehrler et al. |
| 7,757,028 | B2 | 7/2010 | Druke et al. |
| 7,788,600 | B2 | 8/2010 | Lau et al. |
| D631,252 | S | 1/2011 | Leslie |
| 7,932,826 | B2 | 4/2011 | Fritchie et al. |
| 7,945,065 | B2 | 5/2011 | Menzl et al. |
| 7,945,342 | B2 | 5/2011 | Tsai et al. |
| 7,982,776 | B2 | 7/2011 | Dunki-Jacobs et al. |
| 7,995,045 | B2 | 8/2011 | Dunki-Jacobs |
| 8,019,094 | B2 | 9/2011 | Hsieh et al. |
| D655,678 | S | 3/2012 | Kobayashi et al. |
| D657,368 | S | 4/2012 | Magee et al. |
| 8,218,279 | B2 | 7/2012 | Liao et al. |
| D664,969 | S | 8/2012 | Williams et al. |
| D665,396 | S | 8/2012 | Williams et al. |
| 8,239,066 | B2 | 8/2012 | Jennings et al. |
| D667,838 | S | 9/2012 | Magee et al. |
| D675,164 | S | 1/2013 | Kobayashi et al. |
| D676,392 | S | 2/2013 | Gassauer |
| D678,196 | S | 3/2013 | Miyauchi et al. |
| D678,304 | S | 3/2013 | Yakoub et al. |
| 8,423,182 | B2 | 4/2013 | Robinson et al. |
| D681,631 | S | 5/2013 | Akana et al. |
| D687,146 | S | 7/2013 | Juzkiw et al. |
| 8,504,136 | B1 | 8/2013 | Sun et al. |
| 8,540,709 | B2 | 9/2013 | Allen |
| 8,567,393 | B2 | 10/2013 | Hickle et al. |
| D704,839 | S | 5/2014 | Juzkiw et al. |
| D706,826 | S | 6/2014 | Mclean |
| 8,795,001 | B1 | 8/2014 | Lam et al. |
| 8,819,581 | B2 | 8/2014 | Nakamura et al. |
| 8,840,609 | B2 | 9/2014 | Stuebe |
| D716,333 | S | 10/2014 | Chotin et al. |
| 8,911,437 | B2 | 12/2014 | Horlle et al. |
| 8,917,513 | B1 | 12/2014 | Hazzard |
| 8,920,186 | B2 | 12/2014 | Shishikura |
| 8,923,012 | B2 | 12/2014 | Kaufman et al. |
| D720,768 | S | 1/2015 | Hong et al. |
| 8,968,296 | B2 | 3/2015 | McPherson |
| 8,986,288 | B2 | 3/2015 | Konishi |
| D727,958 | S | 4/2015 | Ray et al. |
| 9,017,326 | B2 | 4/2015 | DiNardo et al. |
| D729,267 | S | 5/2015 | Yoo et al. |
| 9,055,870 | B2 | 6/2015 | Meador et al. |
| 9,065,394 | B2 | 6/2015 | Lim et al. |
| D736,239 | S | 8/2015 | Maner |
| 9,129,054 | B2 | 9/2015 | Nawana et al. |
| 9,160,853 | B1 | 10/2015 | Daddi et al. |
| 9,168,054 | B2 | 10/2015 | Turner et al. |
| 9,168,091 | B2 | 10/2015 | Janssen et al. |
| D746,318 | S | 12/2015 | Ling et al. |
| 9,198,711 | B2 | 12/2015 | Joseph |
| 9,226,766 | B2 | 1/2016 | Aldridge et al. |
| 9,226,791 | B2 | 1/2016 | McCarthy et al. |
| 9,237,921 | B2 | 1/2016 | Messerly et al. |
| 9,265,429 | B2 | 2/2016 | St. Pierre et al. |
| 9,277,961 | B2 | 3/2016 | Panescu et al. |
| 9,277,969 | B2 | 3/2016 | Brannan et al. |
| 9,281,615 | B1 | 3/2016 | Plaza et al. |
| 9,320,646 | B2 | 4/2016 | Todd et al. |
| D755,806 | S | 5/2016 | Zankowski et al. |
| 9,345,481 | B2 | 5/2016 | Hall et al. |
| 9,345,900 | B2 | 5/2016 | Wu et al. |
| 9,351,653 | B1 | 5/2016 | Harrison |
| D759,677 | S | 6/2016 | Oguntebi |
| D760,782 | S | 7/2016 | Kendler et al. |
| D764,512 | S | 8/2016 | Mcneil et al. |
| 9,427,255 | B2 | 8/2016 | Griffith et al. |
| 9,430,438 | B2 | 8/2016 | Biskup |
| D766,274 | S | 9/2016 | Che et al. |
| D766,981 | S | 9/2016 | Lee et al. |
| 9,463,646 | B2 | 10/2016 | Payne et al. |
| 9,474,565 | B2 | 10/2016 | Shikhman et al. |
| D772,252 | S | 11/2016 | Myers et al. |
| 9,486,271 | B2 | 11/2016 | Dunning |
| 9,491,895 | B2 | 11/2016 | Steeves et al. |
| D775,209 | S | 12/2016 | Henderson |
| 9,532,827 | B2 | 1/2017 | Morgan et al. |
| 9,589,720 | B2 | 3/2017 | Akahane |
| 9,600,031 | B2 | 3/2017 | Kaneko et al. |
| 9,603,277 | B2 | 3/2017 | Morgan et al. |
| D783,675 | S | 4/2017 | Yagisawa et al. |
| D784,270 | S | 4/2017 | Bhattacharya |
| D785,668 | S | 5/2017 | Akana et al. |
| 9,666,974 | B2 | 5/2017 | Bopp |
| D791,819 | S | 7/2017 | Sagawa et al. |
| D792,425 | S | 7/2017 | Che et al. |
| 9,713,503 | B2 | 7/2017 | Goldschmidt |
| 9,715,271 | B2 | 7/2017 | Kaestner |
| D795,281 | S | 8/2017 | Kim et al. |
| D795,293 | S | 8/2017 | Nichols et al. |
| D797,793 | S | 9/2017 | Nichols et al. |
| 9,750,563 | B2 | 9/2017 | Shikhman et al. |
| 9,770,103 | B2 | 9/2017 | Cochran et al. |
| 9,773,093 | B2 | 9/2017 | Bernini et al. |
| D799,524 | S | 10/2017 | Lalor et al. |
| 9,782,214 | B2 | 10/2017 | Houser et al. |
| 9,788,907 | B1 | 10/2017 | Alvi et al. |
| 9,804,977 | B2 | 10/2017 | Ghosh et al. |

(56) References Cited

U.S. PATENT DOCUMENTS

| | | | |
|---|---|---|---|
| D806,721 S | 1/2018 | Fischer |
| 9,867,670 B2 | 1/2018 | Brannan et al. |
| D810,760 S | 2/2018 | Doyle et al. |
| 9,892,564 B1 | 2/2018 | Cvetko et al. |
| 9,907,196 B2 | 2/2018 | Susini et al. |
| D817,997 S | 5/2018 | Von Weihe |
| 9,971,395 B2 | 5/2018 | Chenault et al. |
| 9,974,595 B2 | 5/2018 | Anderson et al. |
| 9,987,068 B2 | 6/2018 | Anderson et al. |
| 9,987,072 B2 | 6/2018 | McPherson |
| 10,028,402 B1 | 7/2018 | Walker |
| 10,039,589 B2 | 8/2018 | Virshek et al. |
| D832,211 S | 10/2018 | Ladd et al. |
| 10,098,527 B2 | 10/2018 | Weisenburgh, II et al. |
| 10,105,470 B2 | 10/2018 | Reasoner et al. |
| 10,109,835 B2 | 10/2018 | Yang |
| D834,541 S | 11/2018 | You et al. |
| 10,117,702 B2 | 11/2018 | Danziger et al. |
| 10,128,612 B1 | 11/2018 | Casto |
| 10,136,954 B2 | 11/2018 | Johnson et al. |
| 10,137,245 B2 | 11/2018 | Melker et al. |
| D835,669 S | 12/2018 | Hong |
| 10,147,148 B2 | 12/2018 | Wu et al. |
| 10,166,061 B2 | 1/2019 | Berry et al. |
| 10,170,205 B2 | 1/2019 | Curd et al. |
| 10,201,365 B2 | 2/2019 | Boudreaux et al. |
| 10,310,697 B2 | 6/2019 | Roberts et al. |
| 10,339,496 B2 | 7/2019 | Matson et al. |
| 10,357,184 B2 | 7/2019 | Crawford et al. |
| 10,386,990 B2 | 8/2019 | Shikhman et al. |
| 10,441,345 B2 | 10/2019 | Aldridge et al. |
| 10,449,004 B2 | 10/2019 | Ferro et al. |
| 10,475,244 B2 | 11/2019 | Cvetko et al. |
| 10,493,287 B2 | 12/2019 | Yoder et al. |
| 10,499,847 B2 | 12/2019 | Latimer et al. |
| 10,499,996 B2 | 12/2019 | de Almeida Barreto |
| 10,523,122 B2 | 12/2019 | Han et al. |
| 10,531,579 B2 | 1/2020 | Hsiao et al. |
| D876,466 S | 2/2020 | Kobayashi et al. |
| 10,561,753 B2 | 2/2020 | Thompson et al. |
| D878,401 S | 3/2020 | Georgallis |
| 10,602,007 B2 | 3/2020 | Takano |
| 10,624,667 B2 | 4/2020 | Faller et al. |
| 10,624,691 B2 | 4/2020 | Wiener et al. |
| 10,675,100 B2 | 6/2020 | Frushour |
| 10,687,884 B2 | 6/2020 | Wiener et al. |
| 10,698,595 B1 | 6/2020 | Saragadam et al. |
| D894,211 S | 8/2020 | Oguchi et al. |
| 10,729,502 B1 | 8/2020 | Wolf et al. |
| 10,743,872 B2 | 8/2020 | Leimbach et al. |
| 10,758,309 B1 | 9/2020 | Chow et al. |
| 10,758,310 B2 | 9/2020 | Shelton, IV et al. |
| 10,772,673 B2 | 9/2020 | Allen, IV et al. |
| 10,878,966 B2 | 12/2020 | Wolf et al. |
| 10,881,399 B2 | 1/2021 | Shelton, IV et al. |
| 10,895,968 B2 | 1/2021 | Thiercelin et al. |
| 10,898,256 B2 | 1/2021 | Yates et al. |
| 10,909,130 B1 | 2/2021 | Scott et al. |
| 10,925,598 B2 | 2/2021 | Scheib et al. |
| 10,932,705 B2 | 3/2021 | Muhsin et al. |
| 10,932,772 B2 | 3/2021 | Shelton, IV et al. |
| 10,950,982 B2 | 3/2021 | Regnier et al. |
| 10,987,176 B2 | 4/2021 | Poltaretskyi et al. |
| 10,989,724 B1 | 4/2021 | Holmes et al. |
| D918,224 S | 5/2021 | Velamuri et al. |
| D918,246 S | 5/2021 | Getman et al. |
| 11,000,270 B2 | 5/2021 | Scheib et al. |
| D923,640 S | 6/2021 | Tsai et al. |
| D924,139 S | 7/2021 | Jayme |
| D924,914 S | 7/2021 | Hayamizu |
| 11,056,244 B2 | 7/2021 | Shelton, IV et al. |
| 11,065,079 B2 | 7/2021 | Wolf et al. |
| 11,071,595 B2 | 7/2021 | Johnson et al. |
| D928,725 S | 8/2021 | Oberkircher et al. |
| D928,726 S | 8/2021 | Asher et al. |

| | | | |
|---|---|---|---|
| 11,079,995 B1 | 8/2021 | Hulbert et al. |
| 11,083,489 B2 | 8/2021 | Fujii et al. |
| 11,116,587 B2 | 9/2021 | Wolf et al. |
| D939,545 S | 12/2021 | Oberkircher et al. |
| D941,849 S | 1/2022 | Knowles et al. |
| 11,218,822 B2 | 1/2022 | Morgan et al. |
| 11,259,793 B2 | 3/2022 | Scheib et al. |
| 11,259,875 B2 | 3/2022 | Boutin et al. |
| 11,272,839 B2 | 3/2022 | Al-Ali et al. |
| 11,284,963 B2 | 3/2022 | Shelton, IV et al. |
| D948,543 S | 4/2022 | Friedland et al. |
| 11,296,540 B2 | 4/2022 | Kirleis et al. |
| 11,298,128 B2 | 4/2022 | Messerly et al. |
| 11,304,763 B2 | 4/2022 | Shelton, IV et al. |
| 11,314,846 B1 | 4/2022 | Colin et al. |
| 11,350,978 B2 | 6/2022 | Henderson et al. |
| 11,369,366 B2 | 6/2022 | Scheib et al. |
| 11,382,699 B2 | 7/2022 | Wassall et al. |
| 11,382,700 B2 | 7/2022 | Calloway et al. |
| 11,419,604 B2 | 8/2022 | Scheib et al. |
| 11,424,027 B2 | 8/2022 | Shelton, IV |
| 11,432,877 B2 | 9/2022 | Nash et al. |
| 11,464,581 B2 | 10/2022 | Calloway |
| 11,471,206 B2 | 10/2022 | Henderson et al. |
| 11,478,820 B2 | 10/2022 | Bales, Jr. et al. |
| 11,504,192 B2 | 11/2022 | Shelton, IV et al. |
| 11,510,720 B2 | 11/2022 | Morgan et al. |
| 11,510,750 B2 | 11/2022 | Dulin et al. |
| D973,676 S | 12/2022 | Knowles et al. |
| D973,694 S | 12/2022 | Hamre et al. |
| 11,559,307 B2 | 1/2023 | Shelton, IV et al. |
| 11,564,678 B2 | 1/2023 | Scheib et al. |
| 11,571,205 B2 | 2/2023 | Scheib et al. |
| 11,576,677 B2 | 2/2023 | Shelton, IV et al. |
| 11,589,888 B2 | 2/2023 | Shelton, IV et al. |
| D980,251 S | 3/2023 | Ahn et al. |
| 11,607,239 B2 | 3/2023 | Swensgard et al. |
| 11,628,006 B2 | 4/2023 | Henderson et al. |
| 11,638,602 B2 | 5/2023 | Henderson et al. |
| 11,659,023 B2 | 5/2023 | Shelton, IV et al. |
| 11,666,368 B2 | 6/2023 | Henderson et al. |
| 11,678,925 B2 | 6/2023 | Henderson et al. |
| 11,684,400 B2 | 6/2023 | Jayme et al. |
| 11,684,401 B2 | 6/2023 | Oberkircher et al. |
| 11,696,789 B2 | 7/2023 | Petre et al. |
| 11,696,790 B2 | 7/2023 | Oberkircher et al. |
| 11,696,791 B2 | 7/2023 | Henderson et al. |
| D994,693 S | 8/2023 | Ro et al. |
| 11,712,280 B2 | 8/2023 | Henderson et al. |
| D1,026,010 S | 5/2024 | Oberkircher et al. |
| 2001/0029315 A1 | 10/2001 | Sakurai et al. |
| 2003/0007321 A1 | 1/2003 | Dayley |
| 2003/0078631 A1 | 4/2003 | Nelson et al. |
| 2003/0199794 A1 | 10/2003 | Sakurai et al. |
| 2003/0199864 A1 | 10/2003 | Eick |
| 2004/0030328 A1 | 2/2004 | Eggers et al. |
| 2004/0059323 A1 | 3/2004 | Sturm et al. |
| 2004/0111045 A1 | 6/2004 | Sullivan et al. |
| 2004/0164983 A1 | 8/2004 | Khozai |
| 2005/0010209 A1 | 1/2005 | Lee et al. |
| 2005/0013459 A1 | 1/2005 | Maekawa |
| 2005/0113823 A1 | 5/2005 | Reschke et al. |
| 2005/0165390 A1 | 7/2005 | Mauti et al. |
| 2005/0229110 A1 | 10/2005 | Gegner et al. |
| 2005/0251233 A1 | 11/2005 | Kanzius |
| 2006/0085049 A1 | 4/2006 | Cory et al. |
| 2006/0136622 A1 | 6/2006 | Rouvelin et al. |
| 2006/0149418 A1 | 7/2006 | Anvari |
| 2006/0235307 A1* | 10/2006 | Boukhny ............ A61F 9/00745 |
| | | 600/471 |
| 2006/0256516 A1 | 11/2006 | Cho |
| 2007/0061393 A1 | 3/2007 | Moore |
| 2007/0063393 A1 | 3/2007 | Vernin et al. |
| 2007/0076363 A1 | 4/2007 | Liang et al. |
| 2007/0282321 A1 | 12/2007 | Shah et al. |
| 2008/0072896 A1 | 3/2008 | Setzer et al. |
| 2008/0129465 A1 | 6/2008 | Rao |
| 2008/0249377 A1 | 10/2008 | Molducci et al. |
| 2008/0316304 A1 | 12/2008 | Claus et al. |

(56) References Cited

U.S. PATENT DOCUMENTS

| | | |
|---|---|---|
| 2009/0036884 A1 | 2/2009 | Gregg et al. |
| 2009/0049522 A1 | 2/2009 | Claus |
| 2009/0131929 A1 | 5/2009 | Shimizu |
| 2009/0216091 A1 | 8/2009 | Arndt |
| 2009/0234352 A1 | 9/2009 | Behnke et al. |
| 2009/0262088 A1 | 10/2009 | Moll-carrillo et al. |
| 2010/0036405 A1 | 2/2010 | Giordano et al. |
| 2010/0069939 A1 | 3/2010 | Konishi |
| 2010/0076453 A1 | 3/2010 | Morris et al. |
| 2010/0092006 A1 | 4/2010 | Rosen |
| 2010/0120266 A1 | 5/2010 | Rimborg |
| 2010/0198200 A1 | 8/2010 | Horvath |
| 2010/0312239 A1 | 12/2010 | Sclig |
| 2011/0092972 A1 | 4/2011 | Allen |
| 2011/0093796 A1 | 4/2011 | Plummer et al. |
| 2011/0106567 A1 | 5/2011 | Asher |
| 2011/0125149 A1 | 5/2011 | El-Galley et al. |
| 2011/0130689 A1 | 6/2011 | Cohen et al. |
| 2011/0238063 A1 | 9/2011 | Gregg |
| 2011/0245630 A1 | 10/2011 | St. Pierre et al. |
| 2011/0273465 A1 | 11/2011 | Konishi et al. |
| 2011/0288451 A1 | 11/2011 | Sanai et al. |
| 2011/0306840 A1 | 12/2011 | Allen et al. |
| 2012/0029304 A1 | 2/2012 | Medina et al. |
| 2012/0116380 A1 | 5/2012 | Madan et al. |
| 2012/0132661 A1 | 5/2012 | Gu et al. |
| 2012/0319890 A1 | 12/2012 | McCormack et al. |
| 2013/0031201 A1 | 1/2013 | Kagan et al. |
| 2013/0176220 A1 | 7/2013 | Merschon et al. |
| 2013/0197503 A1 | 8/2013 | Orszulak |
| 2013/0267975 A1 | 10/2013 | Timm et al. |
| 2013/0268283 A1 | 10/2013 | Vann et al. |
| 2014/0009894 A1 | 1/2014 | Yu |
| 2014/0058714 A1 | 2/2014 | Boyer |
| 2014/0087573 A1 | 3/2014 | Kroeckel |
| 2014/0108048 A1 | 4/2014 | Cohn |
| 2014/0155721 A1 | 6/2014 | Hauck et al. |
| 2014/0194683 A1 | 7/2014 | Nakaguchi |
| 2014/0226572 A1 | 8/2014 | Thota et al. |
| 2014/0262598 A1 | 9/2014 | Miki et al. |
| 2014/0263552 A1 | 9/2014 | Hall et al. |
| 2014/0378958 A1 | 12/2014 | Leussler |
| 2015/0190189 A1 | 7/2015 | Yates et al. |
| 2015/0272575 A1 | 10/2015 | Leimbach et al. |
| 2015/0289929 A1 | 10/2015 | Toth et al. |
| 2015/0300923 A1 | 10/2015 | Halbert |
| 2015/0334879 A1 | 11/2015 | Fricker |
| 2016/0045247 A1 | 2/2016 | Heim et al. |
| 2016/0058286 A1 | 3/2016 | Joshua et al. |
| 2016/0062954 A1 | 3/2016 | Ruff et al. |
| 2016/0074096 A1 | 3/2016 | Lieu |
| 2016/0120591 A1 | 5/2016 | Smith et al. |
| 2016/0199240 A1 | 7/2016 | Newkirk et al. |
| 2016/0225192 A1 | 8/2016 | Jones et al. |
| 2016/0249945 A1 | 9/2016 | Shelton, IV et al. |
| 2016/0287312 A1 | 10/2016 | Tegg et al. |
| 2016/0287337 A1 | 10/2016 | Aram et al. |
| 2017/0000553 A1 | 1/2017 | Wiener et al. |
| 2017/0024978 A1 | 1/2017 | Gulrez et al. |
| 2017/0078455 A1 | 3/2017 | Fisher et al. |
| 2017/0080346 A1 | 3/2017 | Abbas |
| 2017/0086914 A1 | 3/2017 | Wiener et al. |
| 2017/0090507 A1 | 3/2017 | Wiener et al. |
| 2017/0151011 A1 | 6/2017 | Brustad et al. |
| 2017/0189096 A1 | 7/2017 | Danziger et al. |
| 2017/0202595 A1 | 7/2017 | Shelton, IV |
| 2017/0209718 A1 | 7/2017 | Tanis |
| 2017/0251305 A1 | 8/2017 | Fathollahi |
| 2017/0252091 A1 | 9/2017 | Honda |
| 2017/0319259 A1 | 11/2017 | Dunning |
| 2017/0360466 A1 | 12/2017 | Brown et al. |
| 2018/0014872 A1 | 1/2018 | Dickerson |
| 2018/0042659 A1 | 2/2018 | Rupp et al. |
| 2018/0049795 A1 | 2/2018 | Swayze et al. |
| 2018/0065248 A1 | 3/2018 | Barral et al. |
| 2018/0078216 A1 | 3/2018 | Baker et al. |
| 2018/0082480 A1 | 3/2018 | White et al. |
| 2018/0099161 A1 | 4/2018 | Honda |
| 2018/0166809 A1 | 6/2018 | Brogan et al. |
| 2018/0206909 A1 | 7/2018 | Brustad et al. |
| 2018/0221005 A1 | 8/2018 | Hamel et al. |
| 2018/0221100 A1 | 8/2018 | Berry et al. |
| 2018/0228528 A1 | 8/2018 | Fraasch et al. |
| 2018/0262916 A1 | 9/2018 | Polley et al. |
| 2018/0263557 A1 | 9/2018 | Kahlman |
| 2018/0296283 A1 | 10/2018 | Crawford et al. |
| 2018/0333207 A1 | 11/2018 | Moctezuma De la Barrera |
| 2019/0069957 A1 | 3/2019 | Barral et al. |
| 2019/0125455 A1 | 5/2019 | Shelton, IV et al. |
| 2019/0200844 A1 | 7/2019 | Shelton, IV et al. |
| 2019/0200906 A1 | 7/2019 | Shelton, IV et al. |
| 2019/0200981 A1 | 7/2019 | Harris et al. |
| 2019/0201102 A1 | 7/2019 | Shelton, IV et al. |
| 2019/0201140 A1 | 7/2019 | Yates et al. |
| 2019/0201158 A1 | 7/2019 | Shelton, IV et al. |
| 2019/0205566 A1 | 7/2019 | Shelton, IV et al. |
| 2019/0206563 A1 | 7/2019 | Shelton, IV et al. |
| 2019/0224434 A1 | 7/2019 | Silver et al. |
| 2019/0236840 A1 | 8/2019 | Zuckerman et al. |
| 2019/0247141 A1 | 8/2019 | Batchelor et al. |
| 2019/0278262 A1 | 9/2019 | Taylor et al. |
| 2019/0279524 A1 | 9/2019 | Stoyanov et al. |
| 2019/0334782 A1 | 10/2019 | Dellinger et al. |
| 2019/0348169 A1 | 11/2019 | Gibby et al. |
| 2019/0371012 A1 | 12/2019 | Flexman et al. |
| 2020/0004487 A1 | 1/2020 | Hanajima et al. |
| 2020/0015899 A1 | 1/2020 | Scheib et al. |
| 2020/0015900 A1 | 1/2020 | Scheib et al. |
| 2020/0015907 A1 | 1/2020 | Scheib |
| 2020/0015924 A1 | 1/2020 | Scheib et al. |
| 2020/0030044 A1 | 1/2020 | Wang et al. |
| 2020/0038120 A1 | 2/2020 | Ziraknejad et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078077 A1 | 3/2020 | Henderson et al. |
| 2020/0078078 A1 | 3/2020 | Henderson et al. |
| 2020/0078079 A1 | 3/2020 | Morgan et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078083 A1* | 3/2020 | Sprinkle ............. A61B 18/1206 |
| 2020/0078089 A1 | 3/2020 | Henderson et al. |
| 2020/0078106 A1 | 3/2020 | Henderson et al. |
| 2020/0078110 A1 | 3/2020 | Henderson et al. |
| 2020/0078111 A1* | 3/2020 | Oberkircher ........... A61B 18/00 |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1* | 3/2020 | Petre ...................... A61B 34/35 |
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0159313 A1 | 5/2020 | Gibby et al. |
| 2020/0237422 A1 | 7/2020 | Canady |
| 2020/0265398 A1 | 8/2020 | Lembo |
| 2020/0268472 A1 | 8/2020 | Wolf et al. |
| 2020/0305924 A1 | 10/2020 | Carroll |
| 2020/0305945 A1 | 10/2020 | Morgan et al. |
| 2020/0314569 A1 | 10/2020 | Morgan et al. |
| 2020/0342228 A1 | 10/2020 | Prevrhal et al. |
| 2021/0121246 A1 | 4/2021 | Gudalo |
| 2021/0169578 A1 | 6/2021 | Calloway et al. |
| 2021/0196383 A1 | 7/2021 | Shelton, IV et al. |
| 2021/0203889 A1 | 7/2021 | Fung et al. |
| 2021/0212717 A1 | 7/2021 | Yates et al. |
| 2021/0236755 A1 | 8/2021 | King et al. |
| 2021/0264680 A1 | 8/2021 | Cvetko, Ph.D et al. |

(56) References Cited

U.S. PATENT DOCUMENTS

| | | |
|---|---|---|
| 2021/0385889 A1 | 12/2021 | Patel |
| 2022/0032442 A1 | 2/2022 | Sheffield et al. |
| 2022/0104896 A1 | 4/2022 | Shelton, IV et al. |
| 2022/0104897 A1 | 4/2022 | Shelton, IV et al. |
| 2022/0104911 A1 | 4/2022 | Shelton, IV et al. |
| 2022/0151704 A1 | 5/2022 | Nikou |
| 2022/0155910 A1 | 5/2022 | Jeong |
| 2022/0261056 A1 | 8/2022 | Motoi et al. |
| 2022/0313338 A1 | 10/2022 | Carroll et al. |
| 2022/0313341 A1 | 10/2022 | Wiener et al. |
| 2022/0313342 A1 | 10/2022 | Leuck et al. |
| 2022/0313357 A1 | 10/2022 | Geresy et al. |
| 2022/0313369 A1 | 10/2022 | Oberkircher et al. |
| 2022/0313370 A1 | 10/2022 | Morgan et al. |
| 2022/0313371 A1 | 10/2022 | Morgan et al. |
| 2022/0313372 A1 | 10/2022 | Herman et al. |
| 2022/0313373 A1 | 10/2022 | Morgan et al. |
| 2022/0317750 A1 | 10/2022 | Jayme et al. |
| 2022/0317751 A1 | 10/2022 | Samuel et al. |
| 2022/0318179 A1 | 10/2022 | Morgan et al. |
| 2022/0319685 A1 | 10/2022 | Vachon et al. |
| 2022/0319693 A1 | 10/2022 | Oberkircher et al. |
| 2022/0321059 A1 | 10/2022 | Samuel et al. |
| 2022/0322523 A1 | 10/2022 | Jayme et al. |
| 2022/0331013 A1 | 10/2022 | Shelton, IV et al. |
| 2022/0331047 A1 | 10/2022 | Shelton, IV et al. |
| 2022/0331048 A1 | 10/2022 | Shelton, IV et al. |
| 2022/0331049 A1 | 10/2022 | Shelton, IV et al. |
| 2022/0331050 A1 | 10/2022 | Shelton, IV et al. |
| 2022/0331051 A1 | 10/2022 | Shelton, IV et al. |
| 2022/0331052 A1 | 10/2022 | Shelton, IV et al. |
| 2022/0331053 A1 | 10/2022 | Kimball et al. |
| 2022/0331054 A1 | 10/2022 | Kimball et al. |
| 2022/0331056 A1 | 10/2022 | Shelton, IV et al. |
| 2022/0334787 A1 | 10/2022 | Jogan et al. |
| 2022/0335604 A1 | 10/2022 | Vanosdoll et al. |
| 2022/0335660 A1 | 10/2022 | Shelton, IV et al. |
| 2022/0335696 A1 | 10/2022 | Shelton, IV et al. |
| 2022/0336078 A1 | 10/2022 | Wise et al. |
| 2022/0336097 A1 | 10/2022 | Shelton, IV et al. |
| 2022/0337891 A1 | 10/2022 | Burnley et al. |
| 2022/0338049 A1 | 10/2022 | Ross et al. |
| 2022/0365632 A1 | 11/2022 | Preston et al. |
| 2023/0027299 A1 | 1/2023 | Xu et al. |
| 2023/0038130 A1 | 2/2023 | Cvetko et al. |
| 2023/0039037 A1 | 2/2023 | Henderson et al. |
| 2023/0069787 A1 | 3/2023 | Henderson et al. |
| 2023/0072423 A1 | 3/2023 | Osborn et al. |
| 2023/0389796 A1 | 12/2023 | Shelton, IV et al. |
| 2023/0418450 A1 | 12/2023 | Oberkircher |

FOREIGN PATENT DOCUMENTS

| | | | |
|---|---|---|---|
| EP | 0929263 B1 | 7/1999 | |
| EP | 1006892 B1 | 6/2009 | |
| EP | 2942023 A2 | 11/2015 | |
| JP | 2000089850 A | 3/2000 | |
| JP | 2001029353 A | 2/2001 | |
| WO | WO-0112089 A1 | 2/2001 | |
| WO | WO-2008053485 A1 | 5/2008 | |
| WO | WO-2014031800 A1 | 2/2014 | |
| WO | WO-2014071184 A1 | 5/2014 | |
| WO | WO-2015047693 A1 | 4/2015 | |
| WO | WO-2017058617 A2 | 4/2017 | |
| WO | WO-2018116247 A1 | 6/2018 | |
| WO | WO-2019215354 A1 | 11/2019 | |
| WO | 2020051474 A1 | 3/2020 | |
| WO | WO-2021044136 A1 | 3/2021 | |

OTHER PUBLICATIONS

IEEE Std 802.Mar. 2012 (Revision of IEEE Std 802.3-2008, published Dec. 28, 2012.

"ATM-MPLS Network Interworking Version 2.0, af-aic-0178.001" ATM Standard, The ATM Forum Technical Committee, published Aug. 2003.

Zhu et al. "Haptic-feedback smart glove as a creative human-machine interface (HMI) for virtual/augmented reality applications," Sci. Adv, vol. 6, No. 19, May 8, 2020.

Qian, et al., "A Review of Augmented Reality in Robotic-Assisted Surgery", IEEE Transactions on Medical Robotics and Bionics, IEEE, vol. 2, No. 1, pp. 1-16, Feb. 2020.

Yu et al., "Skin-Integrated Wireless Haptic Interfaces for Virtual and Augmented Reality," Nature, vol. 575, pp. 473-479, Nov. 21, 2019.

Li et al., "Wearable Energy Harvesters Generating Electricity From Low-Frequency Human Limb Movement," Microsystems & Nanoengineering (2018), vol. 4(24), 13 pages.

"BOWA ARC 400" Oct. 30, 2018, posted at bowa-medical.com, [site visited Aug. 6, 2021], https://www.bowa-medical.com/tradepro/shopru/artikel/allgemein/BOWA_BRO_11181_ARC400_V2.1_2018_10_30 EN.pdf (Year: 2018).

"Electrosurgical Generator ECONT-0201.3" Mar. 18, 2018, posted at contact- endoscopy.com, [site visited Aug. 6, 2021], https://contact-endoscopy.com/electrosurgical-system (Year: 2018).

International Search Report and Written Opinion, received for PCT Application No. PCT/IB2023/056563, mailed on Sep. 22, 2023, 13 pages.

"Electrosurgery With the Power of Precision", retrieved from https://www.azcuenaga.ar/wp-content/uploads/2015/10/Generador-Valleylab-FX8.pdf, 2 pages, 2015.

"Electrosurgical Generator ESG-300", retrieved from https://www.youtube.com/watch?v=tRFOyghluZY, 4 pages, 2021.

"Road vehicles—Functional safety—Part 1: Vocabulary", International Organization for Standardization, 2018, 13 pages.

International Search Report and Written Opinion, received for PCT Application No. PCT/IB2023/056579, mailed on Aug. 25, 2023, 13 pages.

Natasha, "View Your Favorite Dashboards and Activity Feed", retrived from https://chartio.com/blog/favorites-and-activity-feed/, 2 pages, 2014.

Piontek, Mike, "Delivery Status: Favorites", retrived from https://dribbble.com/shots/ 36521-Delivery-Status-Favorites, 2 pages, 2010.

Unpublished U.S. Appl. No. 29/704,610, filed Jun. 28, 2022, 1 Page.

Unpublished U.S. Appl. No. 29/704,614, mailed on Jun. 28, 2022, 1 Page.

Unpublished U.S. Appl. No. 29/704,616, mailed on Jun. 28, 2022, 1 Page.

Unpublished U.S. Appl. No. 29/704,617, mailed on Jun. 28, 2022, 1 Page.

"Electrosurgical Unit & Ultrasonic Energy Device", retrived from https://korean-electronics.com/2021/03/18/electrosurgical-unit-ultrasonic-energy-device/, 2 page, 2021.

"Equitable Advisors' Events", retrieved from https://web.archive.org/web/20220625135915/https://apps.apple.com/us/app/equitable-advisors-events/id1498108232 1 page, 2022.

"Generating Simplicity—Electrosurgical Generator ESG-300", retrieved from https://www.youtube.com/watch?v=tRFOyghluZY, 1 page, 2017.

"Medtronic Valleylab FT10 Energy Platform", retrieved from https://www.auxomedical.com/products/medtronic-valleylab-ft10-energy-platform/, 2 pages, 2021.

"Search by Nur Asyrof Muhammad on Dribble", retrieved from https://dribbble.com/shots/ 17489923-Search, 3 pages, 2022.

"The Complete Guide to Sonopet iQ", retrieved from https://www.stryker.com/us/en/nse/products/sonopet-iq.html, 3 page, 2021.

Ahmad, Sayeed, "Hiring Platform—Dashboard UI", retrieved from https:// dribbble.com/shots/15930922-Hiring-Platform-Dashboard-UI, 3 pages., 2021.

* cited by examiner

5000

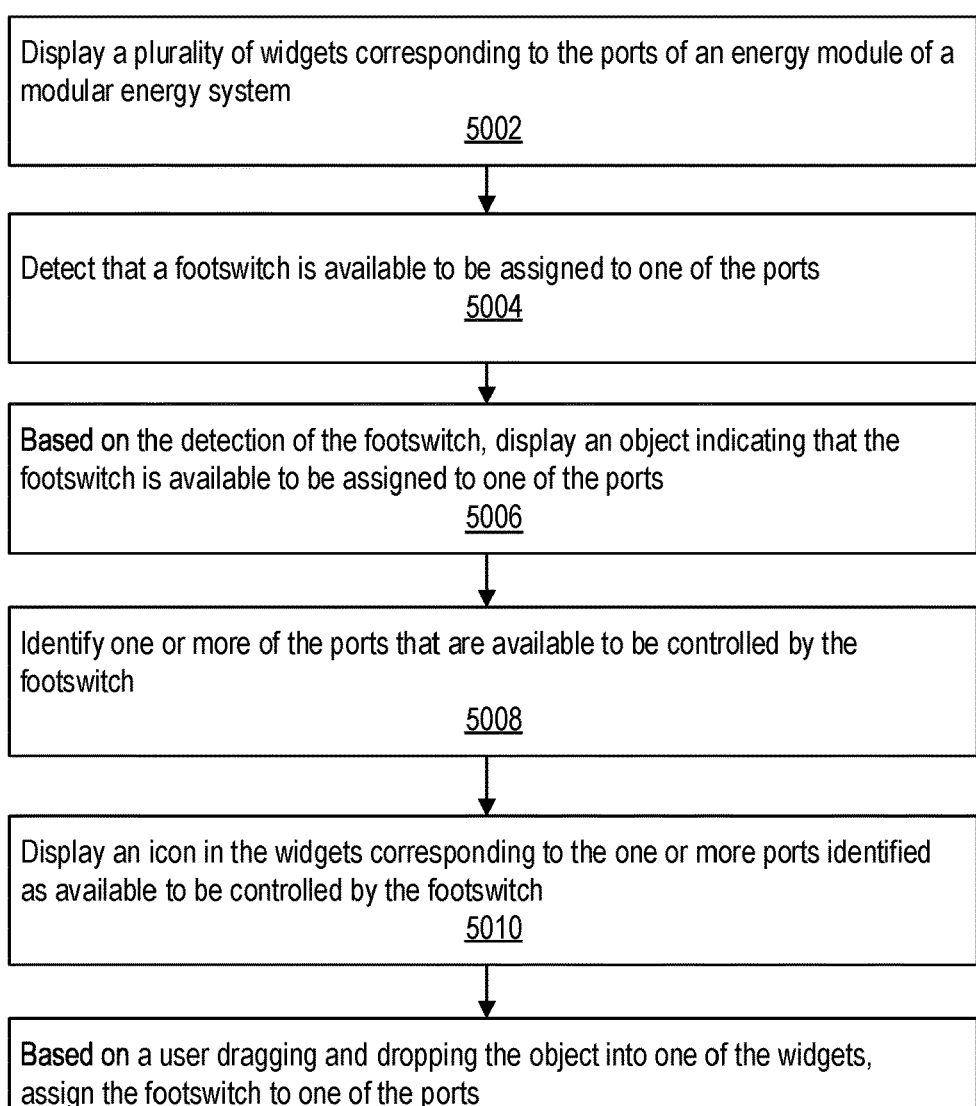

Display a plurality of widgets corresponding to the ports of an energy module of a modular energy system
5002

Detect that a footswitch is available to be assigned to one of the ports
5004

Based on the detection of the footswitch, display an object indicating that the footswitch is available to be assigned to one of the ports
5006

Identify one or more of the ports that are available to be controlled by the footswitch
5008

Display an icon in the widgets corresponding to the one or more ports identified as available to be controlled by the footswitch
5010

Based on a user dragging and dropping the object into one of the widgets, assign the footswitch to one of the ports
5012

FIG. 18

SURGICAL FOOTSWITCH ASSIGNMENT FOR MODULAR ENERGY SYSTEM

BACKGROUND

The present disclosure relates to various surgical systems, including modular electrosurgical and/or ultrasonic energy systems. Modular energy systems can include a variety of different combinations of energy modules each having a variety of different ports for delivering energy modalities to surgical instruments connected thereto. Further, various footswitches can be connected to and used with the modular energy system to control the activation of the ports. Given the different combinations of modules, ports, and footswitches that can be implemented, there is a need for devices, systems, and methods for assigning footswitches to control specific ports of modular energy systems.

SUMMARY

In various aspects, a method for assigning a footswitch to control a port of a modular energy system is disclosed. The modular energy system can include an energy module and a display screen configured to render a graphical user interface (GUI). The energy module can include ports configured to deliver energy modalities to surgical instruments coupled thereto. The method can include displaying, by the GUI, a plurality of widgets corresponding to the ports; detecting, by the modular energy system, a footswitch is available to be assigned to one of the ports; and displaying, by the GUI, an object indicating that the footswitch is available to be assigned to one of the ports based on the detection of the footswitch. The method can further include identifying, by the modular energy system, one or more of the ports that are available to be controlled by the footswitch and displaying, by the GUI, an icon in the widgets corresponding to the one or more ports identified as available to be controlled by the footswitch, wherein the icon indicates that the port is available to be controlled by the footswitch. The method can further include assigning, by the modular energy system, the footswitch to one of the ports based on a user interacting with the GUI to drag and drop the object into one of the widgets having the icon indicating that the port is available to be controlled by the footswitch.

In various aspects, a modular energy system for use in a surgical environment is disclosed. The modular energy system can include one or more energy modules, wherein each of the one or more energy modules comprises ports, and wherein each of the ports is configured to deliver an energy modality to a surgical instrument connected thereto. The system can further include a footswitch configured to control the activation of at least one of the ports and a header module comprising a display screen, wherein the display screen is configured to render a graphical user interface (GUI). The GUI can be configured to: display a plurality of widgets, wherein each widget corresponds to one of the ports; display an object indicating that the footswitch is available to be assigned to one of the ports; display an icon in the widgets corresponding to the ports that are available to be controlled by the footswitch; and allow a user to drag and drop the object into one of the widgets having the icon. Dragging and dropping the object into one of the widgets having the icon can cause the header module to assign the footswitch to the port corresponding to the widget.

FIGURES

The various aspects described herein, both as to organization and methods of operation, together with further objects and advantages thereof, may best be understood by reference to the following description, taken in conjunction with the accompanying drawings as follows.

FIG. 18 is a flow chart of a method for assigning a footswitch to control a port of a modular energy system, in accordance with several aspects of the present disclosure.

Corresponding reference characters indicate corresponding parts throughout the several views. The exemplifications set out herein illustrate various disclosed aspects, in one form, and such exemplifications are not to be construed as limiting the scope thereof in any manner.

DESCRIPTION

Figure 1:
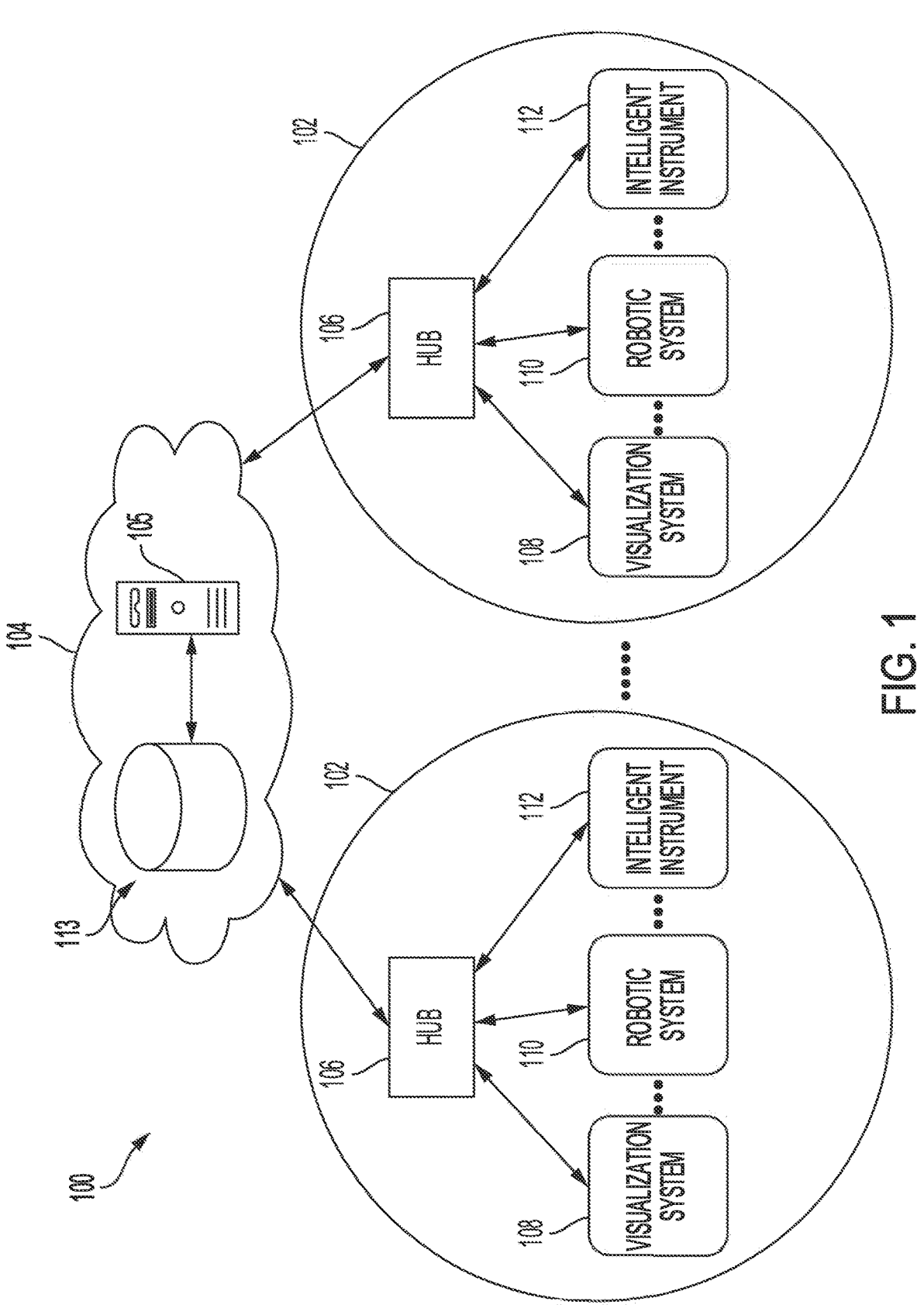
FIG. 1 is a block diagram of a computer-implemented interactive surgical system, in accordance with at least one aspect of the present disclosure.

Applicant of the present application owns the following U.S. Patent Application filed concurrently herewith, the disclosure of which is herein incorporated by reference in its entirety:

3

U.S. patent application Ser. No. 17/851,719, titled PRO-FILES FOR MODULAR ENERGY SYSTEM.

Applicant of the present application owns the following U.S. Patent Applications filed Mar. 30, 2021, the disclosure of each of which is herein incorporated by reference in its entirety:

U.S. patent application Ser. No. 17/217,394, titled METHOD FOR MECHANICAL PACKAGING FOR MODULAR ENERGY SYSTEM;

U.S. patent application Ser. No. 17/217,424, titled METHOD FOR ENERGY DELIVERY FOR MODU-LAR ENERGY SYSTEM;

U.S. patent application Ser. No. 17/217,385, titled METHOD FOR INTELLIGENT INSTRUMENTS FOR MODULAR ENERGY SYSTEM; and U.S. patent application Ser. No. 17/217,405, titled METHOD FOR SYSTEM ARCHITECTURE FOR MODULAR ENERGY SYSTEM.

Applicant of the present application owns the following U.S. Patent Applications filed Sep. 5, 2019, the disclosure of each of which is herein incorporated by reference in its entirety:

U.S. patent application Ser. No. 16/562,144, titled METHOD FOR CONTROLLING A MODULAR ENERGY SYSTEM USER INTERFACE, now U.S. Patent Application Publication No. 2020/0078106;

U.S. patent application Ser. No. 16/562,151, titled PAS-SIVE HEADER MODULE FOR A MODULAR ENERGY SYSTEM, now U.S. Patent Application Pub-lication No. 2020/0078110;

U.S. patent application Ser. No. 16/562,157, titled CON-SOLIDATED USER INTERFACE FOR MODULAR ENERGY SYSTEM, now U.S. Patent Application Pub-lication No. 2020/0081585;

U.S. patent application Ser. No. 16/562,159, titled AUDIO TONE CONSTRUCTION FOR AN ENERGY MODULE OF A MODULAR ENERGY SYSTEM, now U.S. Patent Application Publication No. 2020/0314569;

U.S. patent application Ser. No. 16/562,163, titled ADAPTABLY CONNECTABLE AND REASSIGN-ABLE SYSTEM ACCESSORIES FOR MODULAR ENERGY SYSTEM, now U.S. Patent Application Pub-lication No. 2020/0078111;

U.S. patent application Ser. No. 16/562,123, titled METHOD FOR CONSTRUCTING AND USING A MODULAR SURGICAL ENERGY SYSTEM WITH MULTIPLE DEVICES, now U.S. Patent Application Publication No. 2020/0100830;

U.S. patent application Ser. No. 16/562,135, titled METHOD FOR CONTROLLING AN ENERGY MODULE OUTPUT, now U.S. Patent Application Publication No. 2020/0078076;

U.S. patent application Ser. No. 16/562,180, titled ENERGY MODULE FOR DRIVING MULTIPLE ENERGY MODALITIES, now U.S. Patent Applica-tion Publication No. 2020/0078080;

U.S. patent application Ser. No. 16/562,184, titled GROUNDING ARRANGEMENT OF ENERGY MODULES, now U.S. Patent Application Publication No. 2020/0078081;

U.S. patent application Ser. No. 16/562,188, titled BACKPLANE CONNECTOR DESIGN TO CON-NECT STACKED ENERGY MODULES, now U.S. Patent Application Publication No. 2020/0078116;

U.S. patent application Ser. No. 16/562,195, titled ENERGY MODULE FOR DRIVING MULTIPLE

4

ENERGY MODALITIES THROUGH A PORT, now U.S. Patent Application Publication No. 2020/0078117;

U.S. patent application Ser. No. 16/562,202 titled SUR-GICAL INSTRUMENT UTILIZING DRIVE SIGNAL TO POWER SECONDARY FUNCTION, now U.S. Patent Application Publication No. 2020/0078082;

U.S. patent application Ser. No. 16/562,142, titled METHOD FOR ENERGY DISTRIBUTION IN A SURGICAL MODULAR ENERGY SYSTEM, now U.S. Patent Application Publication No. 2020/0078070;

U.S. patent application Ser. No. 16/562,169, titled SUR-GICAL MODULAR ENERGY SYSTEM WITH A SEGMENTED BACKPLANE, now U.S. Patent Appli-cation Publication No. 2020/0078112;

U.S. patent application Ser. No. 16/562,185, titled SUR-GICAL MODULAR ENERGY SYSTEM WITH FOOTER MODULE, now U.S. Patent Application Publication No. 2020/0078115;

U.S. patent application Ser. No. 16/562,203, titled POWER AND COMMUNICATION MITIGATION ARRANGEMENT FOR MODULAR SURGICAL ENERGY SYSTEM, now U.S. Patent Application Pub-lication No. 2020/0078118;

U.S. patent application Ser. No. 16/562,212, titled MODULAR SURGICAL ENERGY SYSTEM WITH MODULE POSITIONAL AWARENESS SENSING WITH VOLTAGE DETECTION, now U.S. Patent Application Publication No. 2020/0078119;

U.S. patent application Ser. No. 16/562,234, titled MODULAR SURGICAL ENERGY SYSTEM WITH MODULE POSITIONAL AWARENESS SENSING WITH TIME COUNTER, now U.S. Patent Application Publication No. 2020/0305945;

U.S. patent application Ser. No. 16/562,243, titled MODULAR SURGICAL ENERGY SYSTEM WITH MODULE POSITIONAL AWARENESS WITH DIGI-TAL LOGIC, now U.S. Patent Application Publication No. 2020/0078120;

U.S. patent application Ser. No. 16/562,125, titled METHOD FOR COMMUNICATING BETWEEN MODULES AND DEVICES IN A MODULAR SUR-GICAL SYSTEM, now U.S. Patent Application Pub-lication No. 2020/0100825;

U.S. patent application Ser. No. 16/562,137, titled FLEX-IBLE HAND-SWITCH CIRCUIT, now U.S. Patent Application Publication No. 2020/0106220;

U.S. patent application Ser. No. 16/562,143, titled FIRST AND SECOND COMMUNICATION PROTOCOL ARRANGEMENT FOR DRIVING PRIMARY AND SECONDARY DEVICES THROUGH A SINGLE PORT, now U.S. Patent Application Publication No. 2020/0090808;

U.S. patent application Ser. No. 16/562,148, titled FLEX-IBLE NEUTRAL ELECTRODE, now U.S. Patent Application Publication No. 2020/0078077;

U.S. patent application Ser. No. 16/562,154, titled SMART RETURN PAD SENSING THROUGH MODULATION OF NEAR FIELD COMMUNICA-TION AND CONTACT QUALITY MONITORING SIGNALS, now U.S. Patent Application Publication No. 2020/0078089;

U.S. patent application Ser. No. 16/562,162, titled AUTO-MATIC ULTRASONIC ENERGY ACTIVATION CIRCUIT DESIGN FOR MODULAR SURGICAL SYSTEMS, now U.S. Patent Application Publication No. 2020/0305924;

U.S. patent application Ser. No. 16/562,167, titled COORDINATED ENERGY OUTPUTS OF SEPARATE BUT CONNECTED MODULES, now U.S. Patent Application Publication No. 2020/0078078;

U.S. patent application Ser. No. 16/562,170, titled MANAGING SIMULTANEOUS MONOPOLAR OUTPUTS USING DUTY CYCLE AND SYNCHRONIZATION, now U.S. Patent Application Publication No. 2020/0078079;

U.S. patent application Ser. No. 16/562,172, titled PORT PRESENCE DETECTION SYSTEM FOR MODULAR ENERGY SYSTEM, now U.S. Patent Application Publication No. 2020/0078113;

U.S. patent application Ser. No. 16/562,175, titled INSTRUMENT TRACKING ARRANGEMENT BASED ON REAL TIME CLOCK INFORMATION, now U.S. Patent Application Publication No. 2020/0078071;

U.S. patent application Ser. No. 16/562,177, titled REGIONAL LOCATION TRACKING OF COMPONENTS OF A MODULAR ENERGY SYSTEM, now U.S. Patent Application Publication No. 2020/0078114;

U.S. Design Patent Application Ser. No. 29/704,610, titled ENERGY MODULE;

U.S. Design Patent Application Ser. No. 29/704,614, titled ENERGY MODULE MONOPOLAR PORT WITH FOURTH SOCKET AMONG THREE OTHER SOCKETS;

U.S. Design Patent Application Ser. No. 29/704,616, titled BACKPLANE CONNECTOR FOR ENERGY MODULE; and U.S. Design Patent Application Ser. No. 29/704,617, titled ALERT SCREEN FOR ENERGY MODULE.

Applicant of the present application owns the following U.S. Patent Provisional Applications filed Mar. 29, 2019, the disclosure of each of which is herein incorporated by reference in its entirety:

U.S. Provisional Patent Application Ser. No. 62/826,584, titled MODULAR SURGICAL PLATFORM ELECTRICAL ARCHITECTURE;

U.S. Provisional Patent Application Ser. No. 62/826,587, titled MODULAR ENERGY SYSTEM CONNECTIVITY;

U.S. Provisional Patent Application Ser. No. 62/826,588, titled MODULAR ENERGY SYSTEM INSTRUMENT COMMUNICATION TECHNIQUES; and U.S. Provisional Patent Application Ser. No. 62/826,592, titled MODULAR ENERGY DELIVERY SYSTEM.

Applicant of the present application owns the following U.S. Patent Provisional Application filed Sep. 7, 2018, the disclosure of which is herein incorporated by reference in its entirety:

U.S. Provisional Patent Application Ser. No. 62/728,480, titled MODULAR ENERGY SYSTEM AND USER INTERFACE.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various aspects are directed to improved ultrasonic surgical devices, electrosurgical devices and generators for use therewith. Aspects of the ultrasonic surgical devices can be configured for transecting and/or coagulating tissue during surgical procedures, for example. Aspects of the electrosurgical devices can be configured for transecting, coagulating, scaling, welding and/or desiccating tissue during surgical procedures, for example.

Surgical System Hardware

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 2:
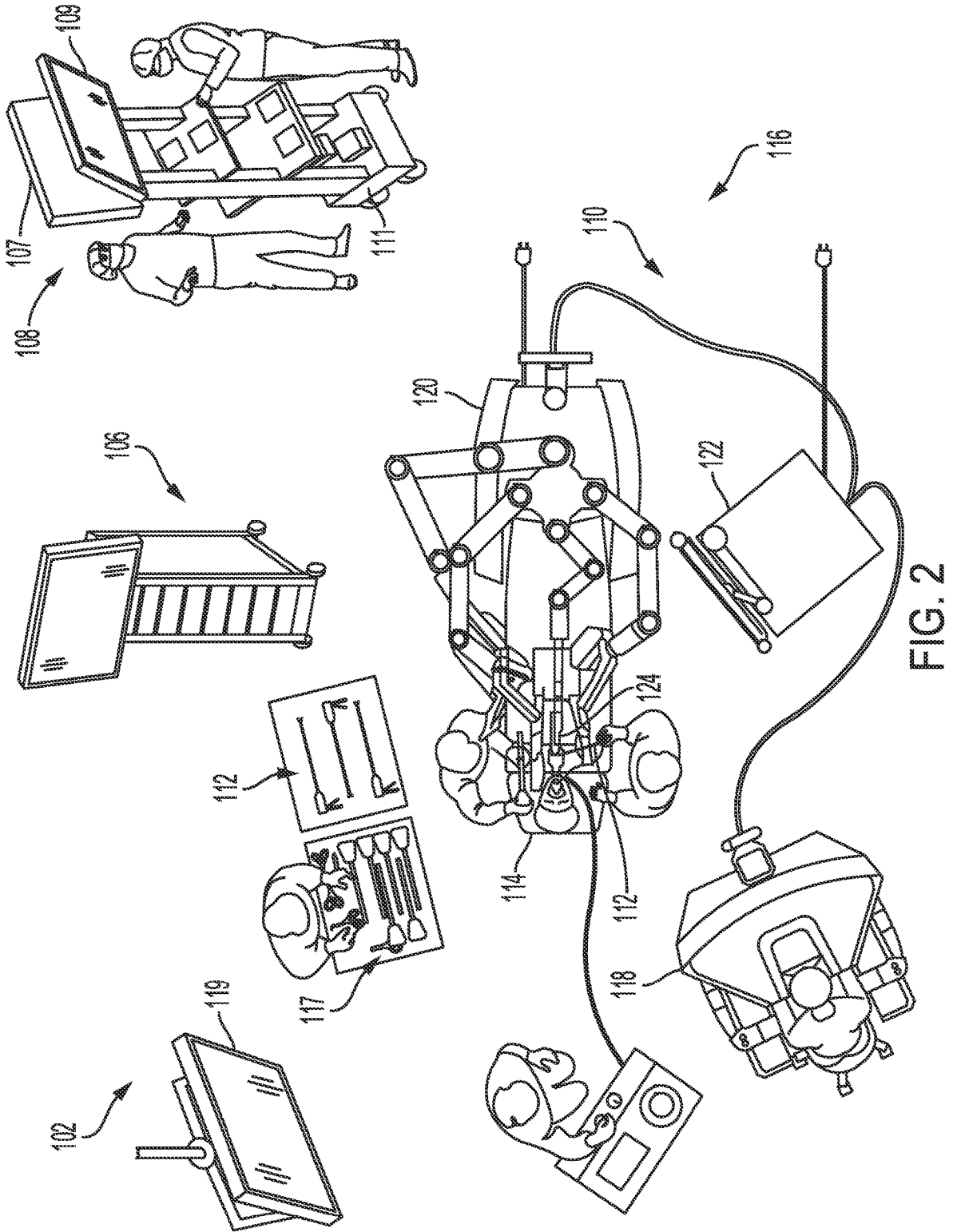
FIG. 2 is a surgical system being used to perform a surgical procedure in an operating room, in accordance with at least one aspect of the present disclosure.

FIG. 2 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and uretero-scope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading SURGICAL INSTRUMENT HARDWARE and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Figure 3:
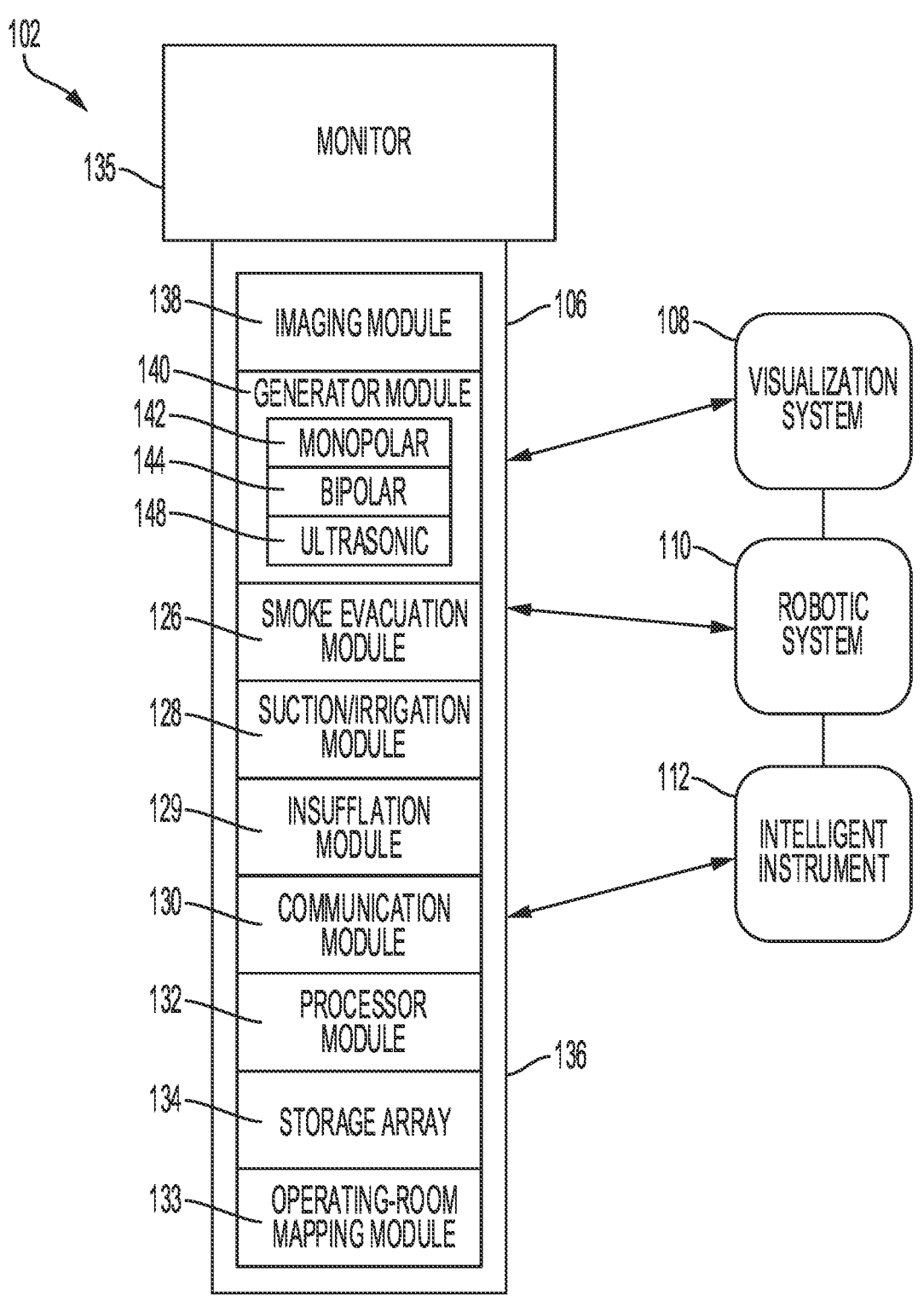
FIG. 3 is a surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. In some aspects, the visualization system 108 may be a separable piece of equipment. In alternative aspects, the visualization system 108 could be contained within the hub 106 as a functional module. The hub 106 includes a hub display 135, an imaging module 138, a generator module 140, a communication module 130, a processor module 132, a storage array 134, and an operating room mapping module 133. In certain aspects, as illustrated in FIG. 3, the hub 106 further includes a smoke evacuation module 126, a suction/irrigation module 128, and/or an insufflation module 129. In certain aspects, any of the modules in the hub 106 may be combined with each other into a single module.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes one or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts. In one aspect, the first energy-generator module is slidably movable into an electrical engagement with the power and data contacts and wherein the first energy-generator module is slidably movable out of the electrical engagement with the first power and data contacts. In an alternative aspect, the first energy-generator module is stackably movable into an electrical engagement with the power and data contacts and wherein the first energy-generator module is stackably movable out of the electrical engagement with the first power and data contacts.

Further to the above, the modular surgical enclosure also includes a second energy-generator module configured to generate a second energy, either the same or different than the first energy, for application to the tissue, and a second docking station comprising a second docking port that includes second data and power contacts. In one aspect, the second energy-generator module is slidably movable into an electrical engagement with the power and data contacts, and wherein the second energy-generator module is slidably movable out of the electrical engagement with the second power and data contacts. In an alternative aspect, the second energy-generator module is stackably movable into an electrical engagement with the power and data contacts, and wherein the second energy-generator module is stackably movable out of the electrical engagement with the second power and data contacts.

In addition, the modular surgical enclosure also includes a communication bus between the first docking port and the second docking port, configured to facilitate communication between the first energy-generator module and the second energy-generator module.

Referring to FIG. 3, aspects of the present disclosure are presented for a hub modular enclosure 136 that allows the modular integration of a generator module 140, a smoke evacuation module 126, a suction/irrigation module 128, and an insufflation module 129. The hub modular enclosure 136 further facilitates interactive communication between the modules 140, 126, 128, 129. The generator module 140 can be a generator module with integrated monopolar, bipolar, and ultrasonic components supported in a single housing unit slidably insertable into the hub modular enclosure 136. The generator module 140 can be configured to connect to a monopolar device 142, a bipolar device 144, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128, 129 and interactive communication therebetween.

Generator Hardware

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions—all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; a SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM.

Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include the modules (as described in connection with FIG. 3, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

Figure 4:
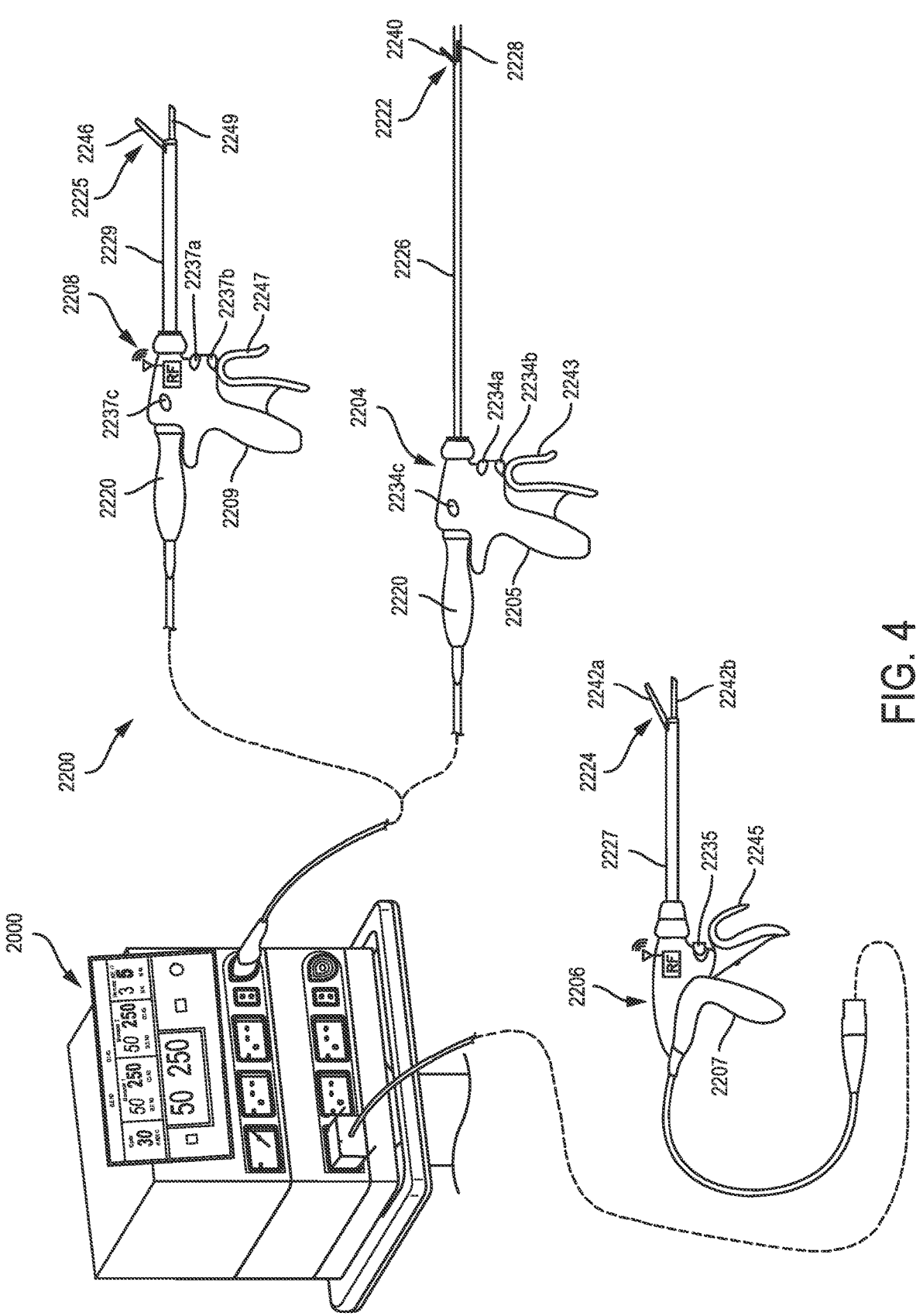
FIG. 4 is a surgical system comprising a generator and various surgical instruments usable therewith, in accordance with at least one aspect of the present disclosure.

FIG. 4 illustrates one form of a surgical system 2200 comprising a modular energy system 2000 and various surgical instruments 2204, 2206, 2208 usable therewith, where the surgical instrument 2204 is an ultrasonic surgical instrument, the surgical instrument 2206 is an RF electrosurgical instrument, and the multifunction surgical instrument 2208 is a combination ultrasonic/RF electrosurgical instrument. The modular energy system 2000 is configurable for use with a variety of surgical instruments. According to various forms, the modular energy system 2000 may be configurable for use with different surgical instruments of different types including, for example, ultrasonic surgical instruments 2204, RF electrosurgical instruments 2206, and multifunction surgical instruments 2208 that integrate RF and ultrasonic energies delivered individually or simultaneously from the modular energy system 2000. Although in the form of FIG. 4 the modular energy system 2000 is shown separate from the surgical instruments 2204, 2206, 2208 in one form, the modular energy system 2000 may be formed integrally with any of the surgical instruments 2204, 2206, 2208 to form a unitary surgical system. The modular energy system 2000 may be configured for wired or wireless communication.

The modular energy system 2000 is configured to drive multiple surgical instruments 2204, 2206, 2208. The first surgical instrument is an ultrasonic surgical instrument 2204 and comprises a handpiece 2205 (HP), an ultrasonic transducer 2220, a shaft 2226, and an end effector 2222. The end effector 2222 comprises an ultrasonic blade 2228 acoustically coupled to the ultrasonic transducer 2220 and a clamp arm 2240. The handpiece 2205 comprises a trigger 2243 to operate the clamp arm 2240 and a combination of the toggle buttons 2234a, 2234b, 2234c to energize and drive the ultrasonic blade 2228 or other function. The toggle buttons 2234a, 2234b, 2234c can be configured to energize the ultrasonic transducer 2220 with the modular energy system 2000.

The modular energy system 2000 also is configured to drive a second surgical instrument 2206. The second surgical instrument 2206 is an RF electrosurgical instrument and comprises a handpiece 2207 (HP), a shaft 2227, and an end effector 2224. The end effector 2224 comprises electrodes in clamp arms 2242a, 2242b and return through an electrical conductor portion of the shaft 2227. The electrodes are coupled to and energized by a bipolar energy source within the modular energy system 2000. The handpiece 2207 comprises a trigger 2245 to operate the clamp arms 2242a, 2242b and an energy button 2235 to actuate an energy switch to energize the electrodes in the end effector 2224.

The modular energy system 2000 also is configured to drive a multifunction surgical instrument 2208. The multifunction surgical instrument 2208 comprises a handpiece 2209 (HP), a shaft 2229, and an end effector 2225. The end effector 2225 comprises an ultrasonic blade 2249 and a clamp arm 2246. The ultrasonic blade 2249 is acoustically coupled to the ultrasonic transducer 2220. The ultrasonic transducer 2220 may be separable from or integral to the handpiece 2209. The handpiece 2209 comprises a trigger 2247 to operate the clamp arm 2246 and a combination of the toggle buttons 2237a, 2237b, 2237c to energize and drive the ultrasonic blade 2249 or other function. The toggle buttons 2237a, 2237b, 2237c can be configured to energize the ultrasonic transducer 2220 with the modular energy system 2000 and energize the ultrasonic blade 2249 with a bipolar energy source also contained within the modular energy system 2000.

The modular energy system 2000 is configurable for use with a variety of surgical instruments. According to various forms, the modular energy system 2000 may be configurable for use with different surgical instruments of different types including, for example, the ultrasonic surgical instrument 2204, the RF electrosurgical instrument 2206, and the multifunction surgical instrument 2208 that integrates RF and ultrasonic energies delivered individually or simultaneously from the modular energy system 2000. Although in the form of FIG. 4 the modular energy system 2000 is shown separate from the surgical instruments 2204, 2206, 2208, in another form the modular energy system 2000 may be formed integrally with any one of the surgical instruments 2204, 2206, 2208 to form a unitary surgical system. Further aspects of generators for digitally generating electrical signal waveforms and surgical instruments are described in U.S. Patent Application Publication No. 2017/0086914, which is herein incorporated by reference in its entirety.

Modular Energy System

ORs everywhere in the world are a tangled web of cords, devices, and people due to the amount of equipment required to perform surgical procedures. Surgical capital equipment tends to be a major contributor to this issue because most surgical capital equipment performs a single, specialized task. Due to their specialized nature and the surgeons' needs to utilize multiple different types of devices during the course of a single surgical procedure, an OR may be forced to be stocked with two or even more pieces of surgical capital equipment, such as energy generators. Each of these pieces of surgical capital equipment must be individually plugged into a power source and may be connected to one or more other devices that are being passed between OR personnel, creating a tangle of cords that must be navigated. Another issue faced in modern ORs is that each of these specialized pieces of surgical capital equipment has its own user interface and must be independently controlled from the other pieces of equipment within the OR. This creates complexity in properly controlling multiple different devices in connection with each other and forces users to be trained on and memorize different types of user interfaces (which may further change based upon the task or surgical procedure being performed, in addition to changing between each piece of capital equipment). This cumbersome, complex process can necessitate the need for even more individuals to be present within the OR and can create danger if multiple devices are not properly controlled in tandem with each other. Therefore, consolidating surgical capital equipment technology into singular systems that are able to flexibly address surgeons' needs to reduce the footprint of surgical capital equipment within ORs would simplify the user experience, reduce the amount of clutter in ORs, and prevent difficulties and dangers associated with simultaneously controlling multiple pieces of capital equipment. Further, making such systems expandable or customizable would allow for new technology to be conveniently incorporated into existing surgical systems, obviating the need to replace entire surgical systems or for OR personnel to learn new user interfaces or equipment controls with each new technology.

As described in FIGS. 1-3, a surgical hub 106 can be configured to interchangeably receive a variety of modules, which can in turn interface with surgical devices (e.g., a surgical instrument or a smoke evacuator) or provide various other functions (e.g., communications). In one aspect, a surgical hub 106 can be embodied as a modular energy system 2000, which is illustrated in connection with FIGS. 5-8. The modular energy system 2000 can include a variety of different modules 2001 that are connectable together in a stacked configuration. In one aspect, the modules 2001 can be both physically and communicably coupled together when stacked or otherwise connected together into a singular assembly. Further, the modules 2001 can be interchangeably connectable together in different combinations or arrangements. In one aspect, each of the modules 2001 can include a consistent or universal array of connectors disposed along their upper and lower surfaces, thereby allowing any module 2001 to be connected to another module 2001 in any arrangement (except that, in some aspects, a particular module type, such as the header module 2002, can be configured to serve as the uppermost module within the stack, for example). In an alternative aspect, the modular energy system 2000 can include a housing that is configured to receive and retain the modules 2001, as is shown in FIG. 3. The modular energy system 2000 can also include a variety of different components or accessories that are also connectable to or otherwise associatable with the modules 2001. In another aspect, the modular energy system 2000 can be embodied as a generator module 140 (FIG. 3) of a surgical hub 106. In yet another aspect, the modular energy system 2000 can be a distinct system from a surgical hub 106. In such aspects, the modular energy system 2000 can be communicably couplable to a surgical hub 206 for transmitting and/or receiving data therebetween.

Figure 5:
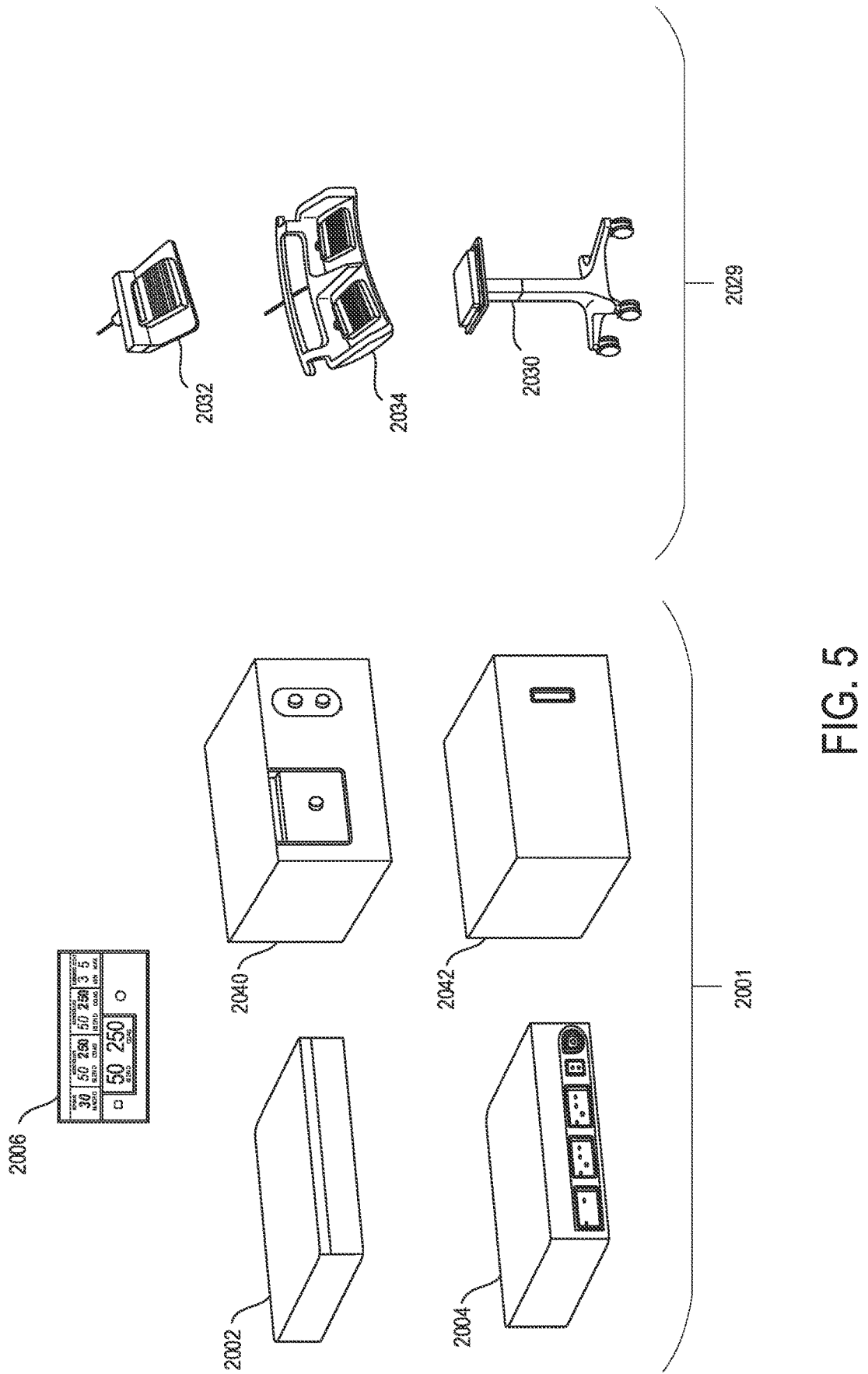
FIG. 5 is a diagram of various modules and other components that are combinable to customize modular energy systems, in accordance with at least one aspect of the present disclosure.

The modular energy system 2000 can be assembled from a variety of different modules 2001, some examples of which are illustrated in FIG. 5. Each of the different types of modules 2001 can provide different functionality, thereby allowing the modular energy system 2000 to be assembled into different configurations to customize the functions and capabilities of the modular energy system 2000 by customizing the modules 2001 that are included in each modular energy system 2000. The modules 2001 of the modular energy system 2000 can include, for example, a header module 2002 (which can include a display screen 2006), an energy module 2004, a technology module 2040, and a visualization module 2042. In the depicted aspect, the header module 2002 is configured to serve as the top or uppermost module within the modular energy system stack and can thus lack connectors along its top surface. In another aspect, the header module 2002 can be configured to be positioned at the bottom or the lowermost module within the modular energy system stack and can thus lack connectors along its bottom surface. In yet another aspect, the header module 2002 can be configured to be positioned at an intermediate position within the modular energy system stack and can thus include connectors along both its bottom and top surfaces. The header module 2002 can be configured to control the system-wide settings of each module 2001 and component connected thereto through physical controls 2011 thereon and/or a graphical user interface (GUI) 2008 rendered on the display screen 2006. Such settings could include the activation of the modular energy system 2000, the volume of alerts, the footswitch settings, the settings icons, the appearance or configuration of the user interface, the surgeon profile logged into the modular energy system 2000, and/or the type of surgical procedure being performed. The header module 2002 can also be configured to provide communications, processing, and/or power for the modules 2001 that are connected to the header module 2002. The energy module 2004, which can also be referred to as a generator module 140 (FIG. 3), can be configured to generate one or multiple energy modalities for driving electrosurgical and/or ultrasonic surgical instruments connected thereto. The technology module 2040 can be configured to provide additional or expanded control algorithms (e.g., electrosurgical or ultrasonic control algorithms for controlling the energy output of the energy module 2004). The visualization module 2042 can be configured to interface with visualization devices (i.e., scopes) and accordingly provide increased visualization capabilities.

The modular energy system 2000 can further include a variety of accessories 2029 that are connectable to the modules 2001 for controlling the functions thereof or that are otherwise configured to work on conjunction with the modular energy system 2000. The accessories 2029 can include, for example, a single-pedal footswitch 2032, a dual-pedal footswitch 2034, and a cart 2030 for supporting the modular energy system 2000 thereon. The footswitches 2032, 2034 can be configured to control the activation or function of particular energy modalities output by the energy module 2004, for example.

By utilizing modular components, the depicted modular energy system 2000 provides a surgical platform that grows with the availability of technology and is customizable to the needs of the facility and/or surgeons. Further, the modular energy system 2000 supports combo devices (e.g., dual electrosurgical and ultrasonic energy generators) and supports software-driven algorithms for customized tissue effects. Still further, the surgical system architecture reduces the capital footprint by combining multiple technologies critical for surgery into a single system.

The various modular components utilizable in connection with the modular energy system 2000 can include monopolar energy generators, bipolar energy generators, dual electrosurgical/ultrasonic energy generators, display screens, and various other modules and/or other components, some of which are also described above in connection with FIGS. 1-3.

Figure 6B:
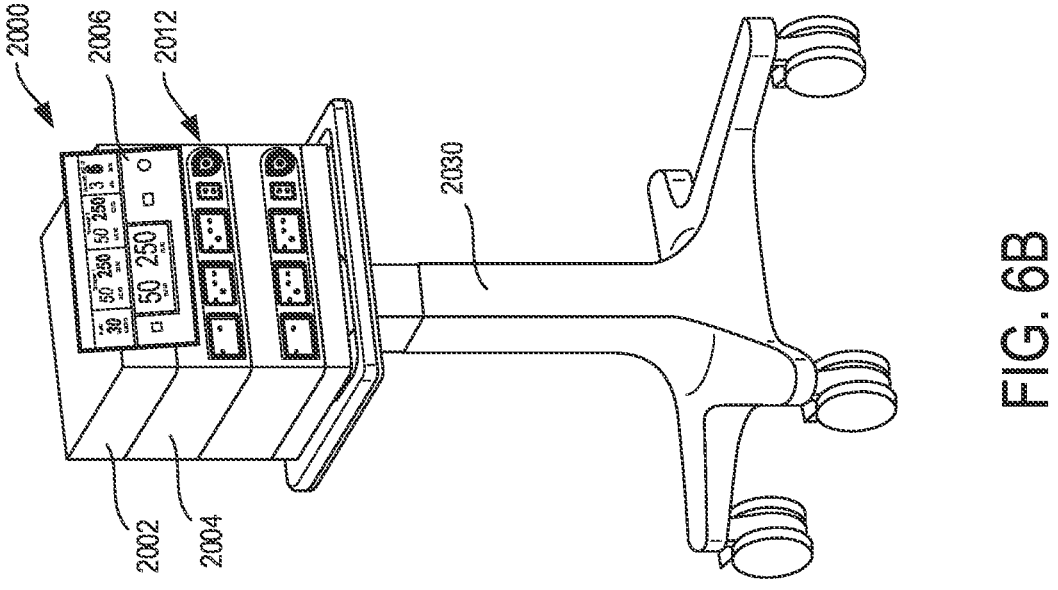
FIG. 6B is the modular energy system shown in FIG. 6A mounted to a cart, in accordance with at least one aspect of the present disclosure.
Figure 6A:
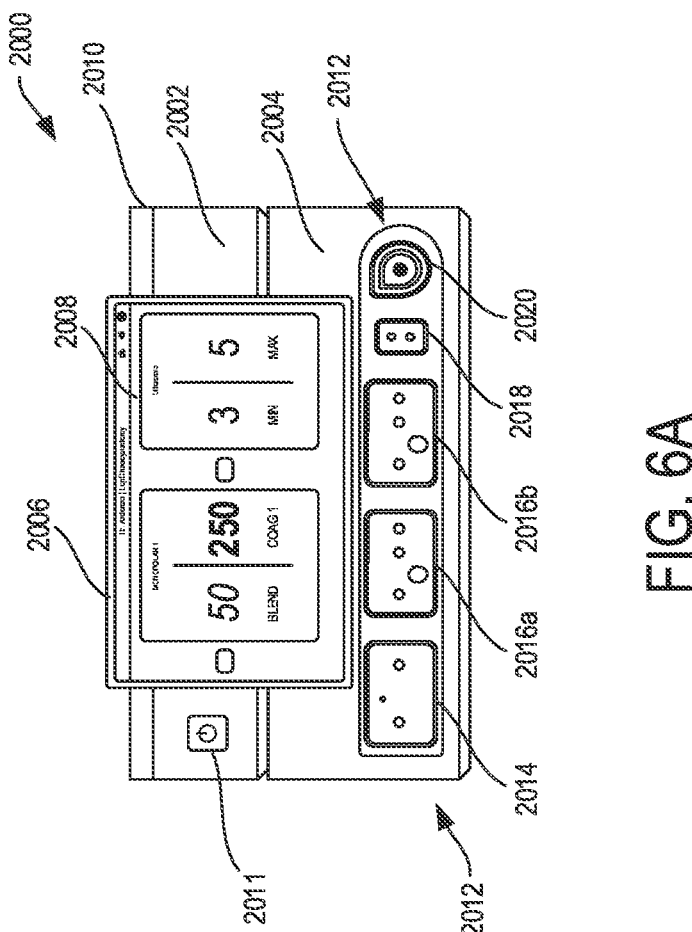
FIG. 6A is a first illustrative modular energy system configuration including a header module and a display screen that renders a graphical user interface (GUI) for relaying information regarding modules connected to the header module, in accordance with at least one aspect of the present disclosure.

Referring now to FIG. 6A, the header module 2002 can, in some aspects, include a display screen 2006 that renders a GUI 2008 for relaying information regarding the modules 2001 connected to the header module 2002. In some aspects, the GUI 2008 of the display screen 2006 can provide a consolidated point of control of all of the modules 2001 making up the particular configuration of the modular energy system 2000. Various aspects of the GUI 2008 are discussed in fuller detail below in connection with FIG. 8. In alternative aspects, the header module 2002 can lack the display screen 2006 or the display screen 2006 can be detachably connected to the housing 2010 of the header module 2002. In such aspects, the header module 2002 can be communicably couplable to an external system that is configured to display the information generated by the modules 2001 of the modular energy system 2000. For example, in robotic surgical applications, the modular energy system 2000 can be communicably couplable to a robotic cart or robotic control console, which is configured to display the information generated by the modular energy system 2000 to the operator of the robotic surgical system. As another example, the modular energy system 2000 can be communicably couplable to a mobile display that can be carried or secured to a surgical staff member for viewing thereby. In aspects utilizing a user interface that is separate from or otherwise distinct from the modular energy system 2000, the user interface can be wirelessly connectable with the modular energy system 2000 as a whole or one or more modules 2001 thereof such that the user interface can display information from the connected modules 2001 thereon.

Referring still to FIG. 6A, the energy module 2004 can include a port assembly 2012 including a number of different ports configured to deliver different energy modalities to corresponding surgical instruments that are connectable thereto. In the particular aspect illustrated in FIGS. 5-8, the port assembly 2012 includes a bipolar port 2014, a first monopolar port 2016a, a second monopolar port 2016b, a neutral electrode port 2018 (to which a monopolar return pad is connectable), and a combination energy port 2020. However, this particular combination of ports is simply provided for illustrative purposes and alternative combinations of ports and/or energy modalities may be possible for the port assembly 2012.

As noted above, the modular energy system 2000 can be assembled into different configurations. Further, the different configurations of the modular energy system 2000 can also be utilizable for different surgical procedure types and/or different tasks. For example, FIGS. 6A and 6B illustrate a first illustrative configuration of the modular energy system 2000 including a header module 2002 (including a display screen 2006) and an energy module 2004 connected together. Such a configuration can be suitable for laparoscopic and open surgical procedures, for example.

Figure 7:
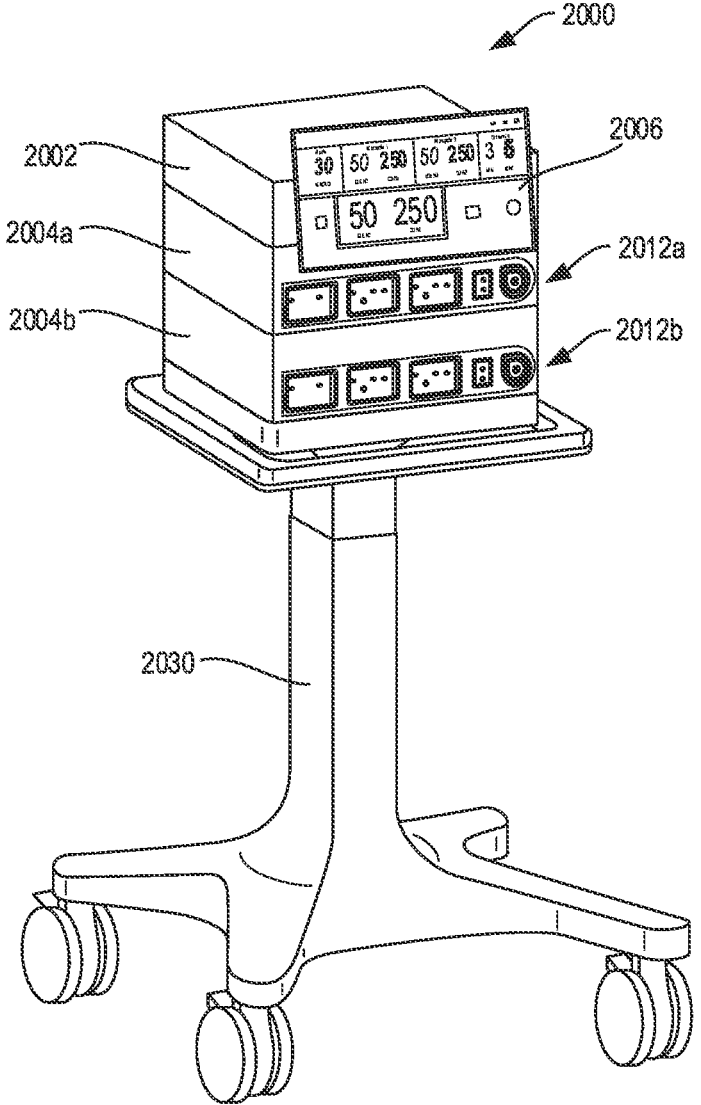
FIG. 7 is a second illustrative modular energy system configuration including a header module, a display screen, an energy module, and an expanded energy module connected together and mounted to a cart, in accordance with at least one aspect of the present disclosure.

FIG. 7 illustrates a second illustrative configuration of the modular energy system 2000 including a header module 2002 (including a display screen 2006), a first energy module 2004a, and a second energy module 2004b connected together. By stacking two energy modules 2004a, 2004b, the modular energy system 2000 can provide a pair of port assemblies 2012a, 2012b for expanding the array of energy modalities deliverable by the modular energy system 2000 from the first configuration. The second configuration of the modular energy system 2000 can accordingly accommodate more than one bipolar/monopolar electrosurgical instrument, more than two bipolar/monopolar electrosurgical instruments, and so on. Such a configuration can be suitable for particularly complex laparoscopic and open surgical procedures.

It should be noted that the configurations illustrated in FIGS. 6A-7 and described above are provided simply to illustrate the various concepts of the modular energy system 2000 and should not be interpreted to limit the modular energy system 2000 to the particular aforementioned configurations.

Figure 8:
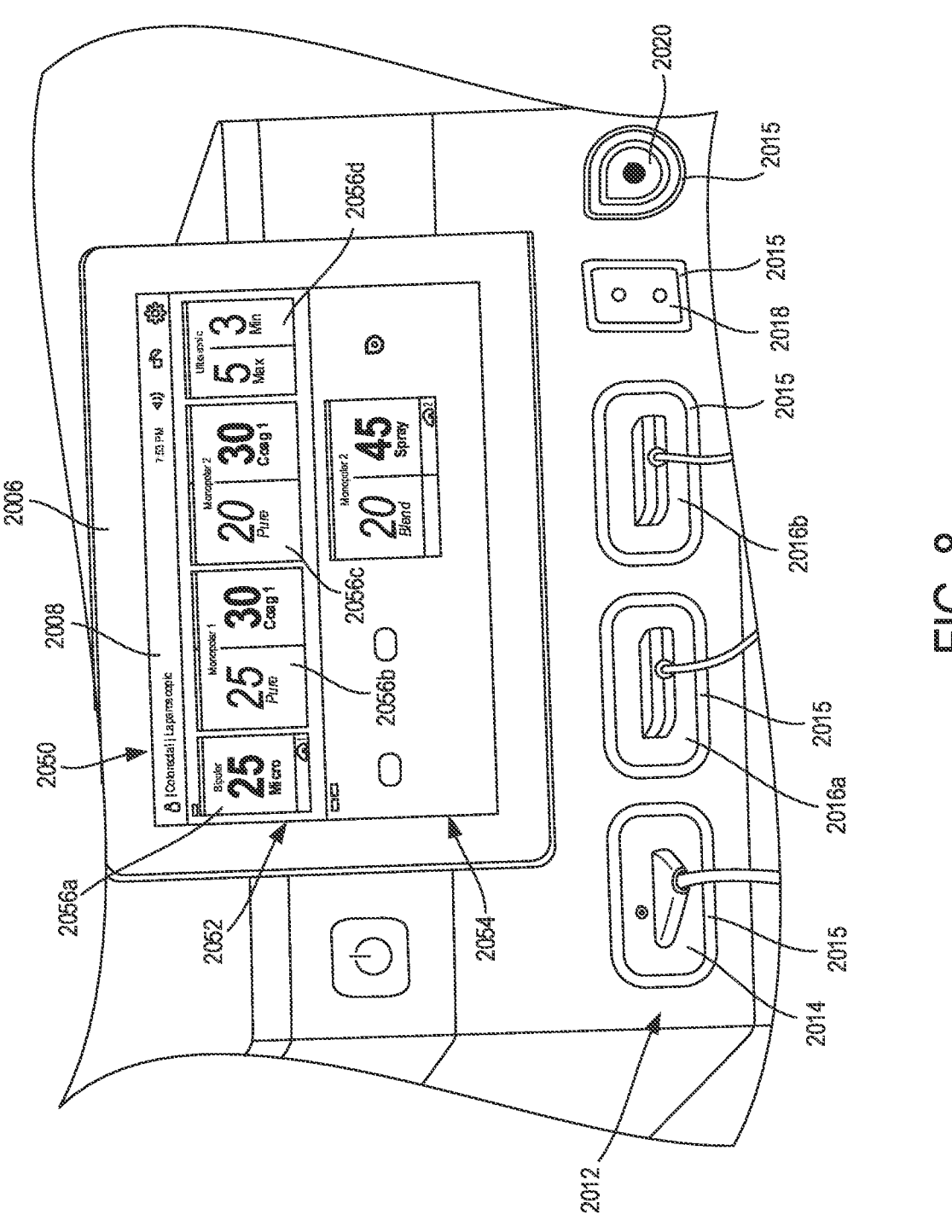
FIG. 8 is a perspective view of a header module of a modular energy system including a user interface, in accordance with at least one aspect of the present disclosure.

Referring now to FIG. 8, in some aspects, the header module 2002 can include or support a display 2006 configured for displaying a GUI 2008, as noted above. The display screen 2006 can include a touchscreen for receiving input from users in addition to displaying information. The controls displayed on the GUI 2008 can correspond to the module(s) 2001 that are connected to the header module 2002. In some aspects, different portions or areas of the GUI 2008 can correspond to particular modules 2001. For example, a first portion or area of the GUI 2008 can correspond to a first module and a second portion or area of the GUI 2008 can correspond to a second module. As different and/or additional modules 2001 are connected to the modular energy system stack, the GUI 2008 can adjust to accommodate the different and/or additional controls for each newly added module 2001 or remove controls for each module 2001 that is removed. Each portion of the display corresponding to a particular module connected to the header module 2002 can display controls, data, user prompts, and/or other information corresponding to that module. For example, in FIG. 12, a first or upper portion 2052 of the depicted GUI 2008 displays controls and data associated with an energy module 2004 that is connected to the header module 2002. In particular, the first portion 2052 of the GUI 2008 for the energy module 2004 provides first widget 2056*a* corresponding to the bipolar port 2014, a second widget 2056*b* corresponding to the first monopolar port 2016*a*, a third widget 2056*c* corresponding to the second monopolar port 2016*b*, and a fourth widget 2056*d* corresponding to the combination energy port 2020. Each of these widgets 2056*a-d* provides data related to its corresponding port of the port assembly 2012 and controls for controlling the modes and other features of the energy modality delivered by the energy module 2004 through the respective port of the port assembly 2012. For example, the widgets 2056*a-d* can be configured to display the power level of the surgical instrument connected to the respective port, change the operational mode of the surgical instrument connected to the respective port (e.g., change a surgical instrument from a first power level to a second power level and/or change a monopolar surgical instrument from a "spray" mode to a "blend" mode), and so on.

In one aspect, the header module 2002 can include various physical controls 2011 in addition to or in lieu of the GUI 2008. Such physical controls 2011 can include, for example, a power button that controls the application of power to each module 2001 that is connected to the header module 2002 in the modular energy system 2000. Alternatively, the power button can be displayed as part of the GUI 2008. Therefore, the header module 2002 can serve as a single point of contact and obviate the need to individually activate and deactivate each individual module 2001 from which the modular energy system 2000 is constructed.

In one aspect, the header module 2002 can display still images, videos, animations, and/or information associated with the surgical modules 2001 of which the modular energy system 2000 is constructed or the surgical devices that are communicably coupled to the modular energy system 2000. The still images and/or videos displayed by the header module 2002 can be received from an endoscope or another visualization device that is communicatively coupled to the modular energy system 2000. The animations and/or information of the GUI 2008 can be overlaid on or displayed adjacent to the images or video feed.

In one aspect, the modules 2001 other than the header module 2002 can be configured to likewise relay information to users. For example, the energy module 2004 can include light assemblies 2015 disposed about each of the ports of the port assembly 2012. The light assemblies 2015 can be configured to relay information to the user regarding the port according to their color or state (e.g., flashing). For example, the light assemblies 2015 can change from a first color to a second color when a plug is fully seated within the respective port. In one aspect, the color or state of the light assemblies 2015 can be controlled by the header module 2002. For example, the header module 2002 can cause the light assembly 2015 of each port to display a color corresponding to the color display for the port on the GUI 2008.

Figure 9:
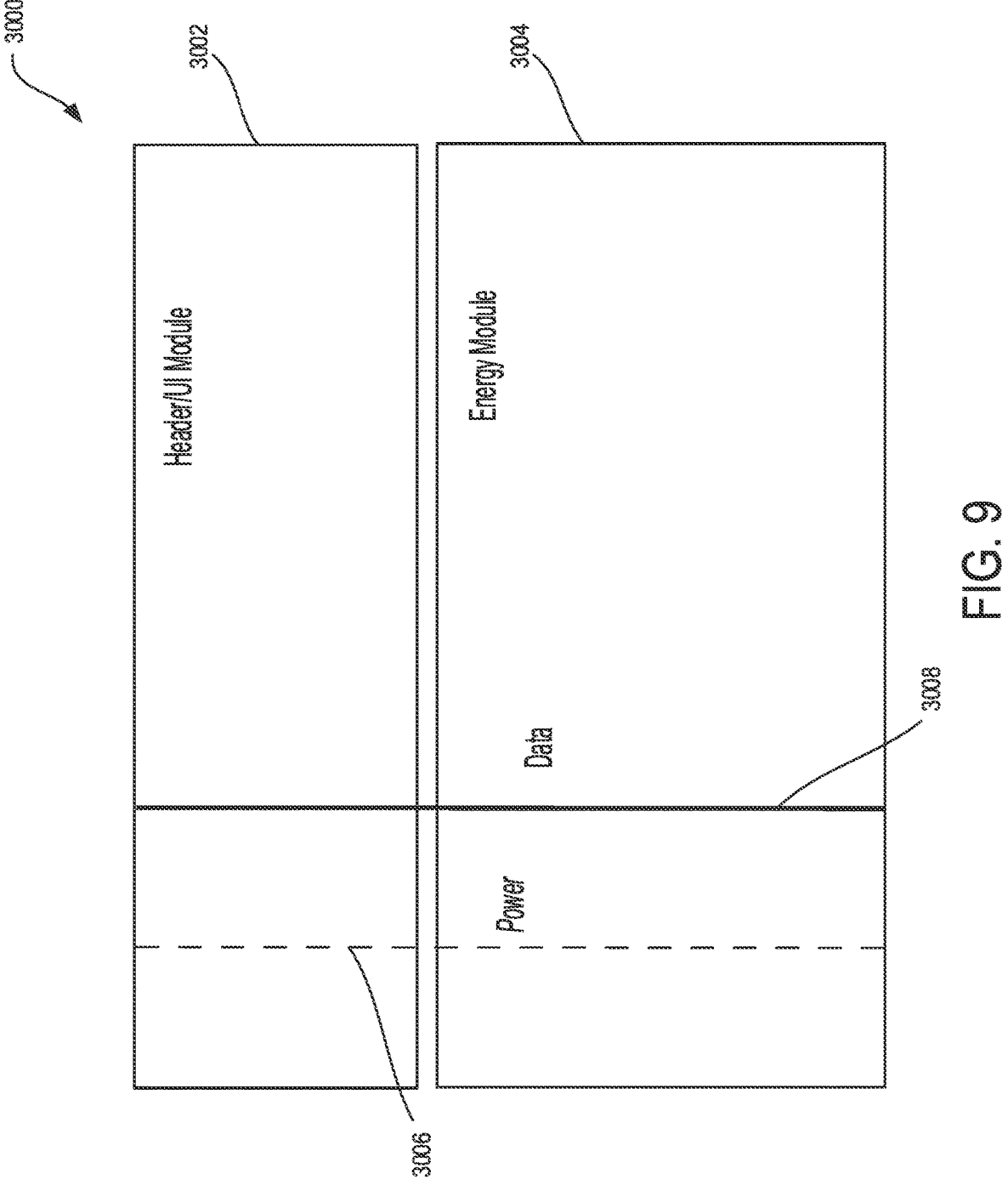
FIG. 9 is a block diagram of a stand-alone hub configuration of a modular energy system, in accordance with at least one aspect of the present disclosure.
Figure 10:
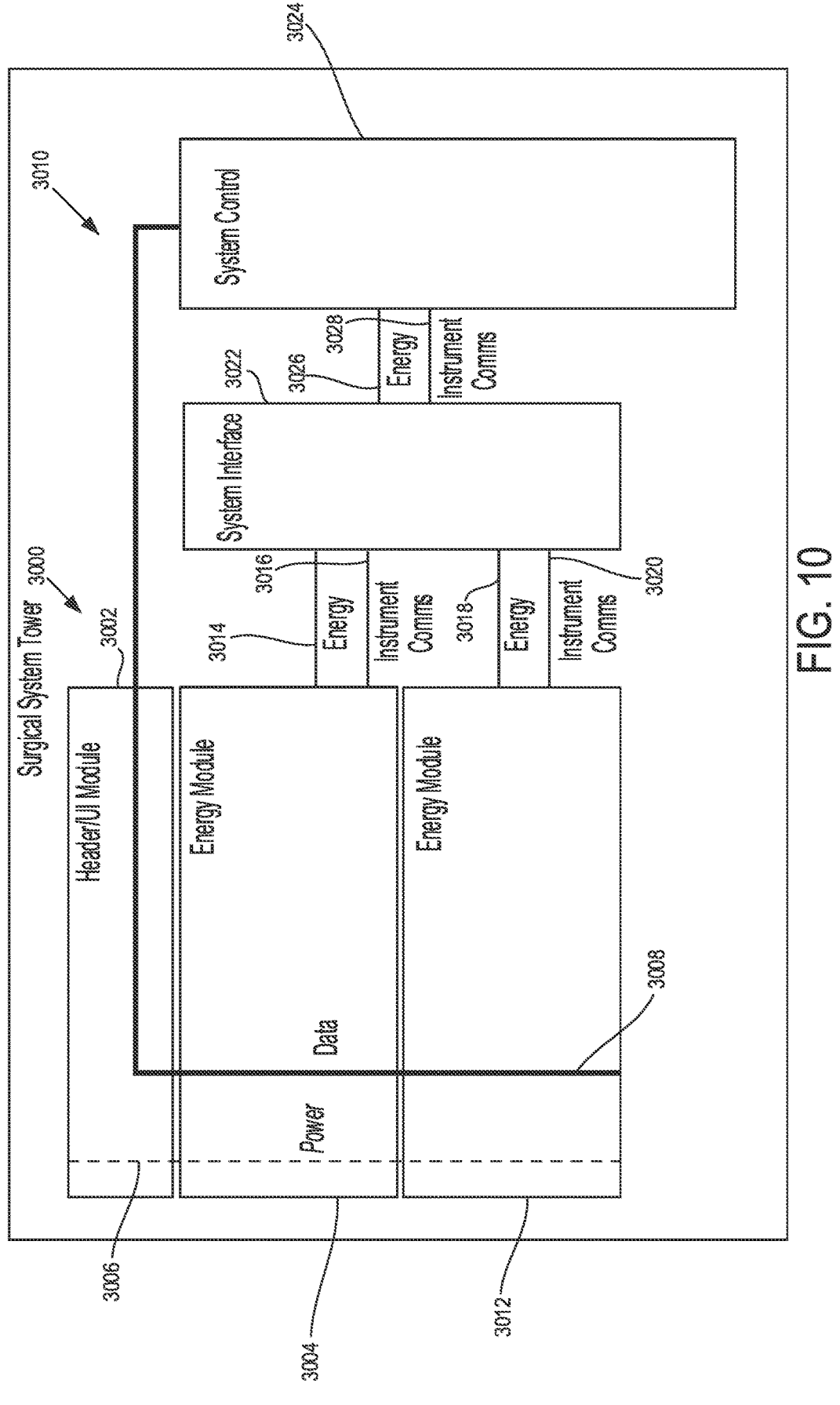
FIG. 10 is a block diagram of a hub configuration of a modular energy system integrated with a surgical control system, in accordance with at least one aspect of the present disclosure.

FIG. 9 is a block diagram of a stand-alone hub configuration of a modular energy system 3000, in accordance with at least one aspect of the present disclosure and FIG. 10 is a block diagram of a hub configuration of a modular energy system 3000 integrated with a surgical control system 3010, in accordance with at least one aspect of the present disclosure. As depicted in FIGS. 9 and 10, the modular energy system 3000 can be either utilized as stand-alone units or integrated with a surgical control system 3010 that controls and/or receives data from one or more surgical hub units. In the examples illustrated in FIGS. 9 and 10, the integrated header/UI module 3002 of the modular energy system 3000 includes a header module and a UI module integrated together as a singular module. In other aspects, the header module and the UI module can be provided as separate components that are communicatively coupled though a data bus 3008.

As illustrated in FIG. 9, an example of a stand-alone modular energy system 3000 includes an integrated header module/user interface (UI) module 3002 coupled to an energy module 3004. Power and data are transmitted between the integrated header/UI module 3002 and the energy module 3004 through a power interface 3006 and a data interface 3008. For example, the integrated header/UI module 3002 can transmit various commands to the energy module 3004 through the data interface 3008. Such commands can be based on user inputs from the UI. As a further example, power may be transmitted to the energy module 3004 through the power interface 3006.

In FIG. 10, a surgical hub configuration includes a modular energy system 3000 integrated with a control system 3010 and an interface system 3022 for managing, among other things, data and power transmission to and/or from the modular energy system 3000. The modular energy system depicted in FIG. 10 includes an integrated header module/UI module 3002, a first energy module 3004, and a second energy module 3012. In one example, a data transmission pathway is established between the system control unit 3024 of the control system 3010 and the second energy module 3012 through the first energy module 3004 and the header/UI module 3002 through a data interface 3008. In addition, a power pathway extends between the integrated header/UI module 3002 and the second energy module 3012 through the first energy module 3004 through a power interface 3006. In other words, in one aspect, the first energy module 3004 is configured to function as a power and data interface between the second energy module 3012 and the integrated header/UI module 3002 through the power interface 3006 and the data interface 3008. This arrangement allows the modular energy system 3000 to expand by seamlessly connecting additional energy modules to energy modules 3004, 3012 that are already connected to the integrated header/UI module 3002 without the need for dedicated power and energy interfaces within the integrated header/UI module 3002.

The system control unit 3024, which may be referred to herein as a control circuit, control logic, microprocessor, microcontroller, logic, or FPGA, or various combinations thereof, is coupled to the system interface 3022 via energy interface 3026 and instrument communication interface 3028. The system interface 3022 is coupled to the first energy module 3004 via a first energy interface 3014 and a first instrument communication interface 3016. The system interface 3022 is coupled to the second energy module 3012 via a second energy interface 3018 and a second instrument communication interface 3020. As additional modules, such as additional energy modules, are stacked in the modular energy system 3000, additional energy and communications interfaces are provided between the system interface 3022 and the additional modules.

The energy modules 3004, 3012 are connectable to a hub and can be configured to generate electrosurgical energy (e.g., bipolar or monopolar), ultrasonic energy, or a combination thereof (referred to herein as an "advanced energy" module) for a variety of energy surgical instruments. Generally, the energy modules 3004, 3012 include hardware/software interfaces, an ultrasonic controller, an advanced energy RF controller, bipolar RF controller, and control algorithms executed by the controller that receives outputs from the controller and controls the operation of the various energy modules 3004, 3012 accordingly. In various aspects of the present disclosure, the controllers described herein may be implemented as a control circuit, control logic, microprocessor, microcontroller, logic, or FPGA, or various combinations thereof.

In one aspect, with reference to FIGS. 9 and 10, the modules of the modular energy system 3000 can include an optical link allowing high speed communication (10-50 Mb/s) across the patient isolation boundary. This link would carry device communications, mitigation signals (watchdog, etc.), and low bandwidth run-time data. In some aspects, the optical link(s) will not contain real-time sampled data, which can be done on the non-isolated side.

In one aspect, with reference to FIGS. 9 and 10, the modules of the modular energy system 3000 can include a multi-function circuit block which can: (i) read presence resistor values via A/D and current source, (ii) communicate with legacy instruments via hand switch Q protocols, (iii) communicate with instruments via local bus 1-Wire protocols, and (iv) communicate with CAN FD-enabled surgical instruments. When a surgical instrument is properly identified by an energy generator module, the relevant pin functions and communications circuits are enabled, while the other unused functions are disabled or disconnected, and set to a high impedance state.

In one aspect, with reference to FIGS. 9 and 10, the modules of the modular energy system 3000 can include a pulse/stimulation/auxiliary amplifier. This is a flexible-use amplifier based on a full-bridge output and incorporates functional isolation. This allows its differential output to be referenced to any output connection on the applied part (except, in some aspects, a monopolar active electrode). The amplifier output can be either small signal linear (pulse/stim) with waveform drive provided by a DAC or a square wave drive at moderate output power for DC applications such as DC motors, illumination, FET drive, etc. The output voltage and current are sensed with functionally isolated voltage and current feedback to provide accurate impedance and power measurements to the FPGA. Paired with a CAN FD-enabled instrument, this output can offer motor/motion control drive, while position or velocity feedback is provided by the CAN FD interface for closed loop control.

As described in greater detail herein, a modular energy system comprises a header module and one or more functional or surgical modules. In various instances, the modular energy system is a modular energy system. In various instances, the surgical modules include energy modules, communication modules, user interface modules; however, the surgical modules are envisioned to be any suitable type of functional or surgical module for use with the modular energy system.

Modular energy system offers many advantages in a surgical procedure, as described above in connection with the modular energy systems 2000 (FIGS. 5-8), 3000 (FIGS. 9-10). However, cable management and setup/teardown time can be a significant deterrent. Various aspects of the present disclosure provide a modular energy system with a single power cable and a single power switch to control startup and shutdown of the entire modular energy system, which obviated the need to individually activate and deactivate each individual module from which the modular energy system is constructed. Also, various aspects of the present disclosure provide a modular energy system with power management schemes that facilitate a safe and, in some instances, concurrent delivery of power to the modules of a modular energy system.

Figure 11:
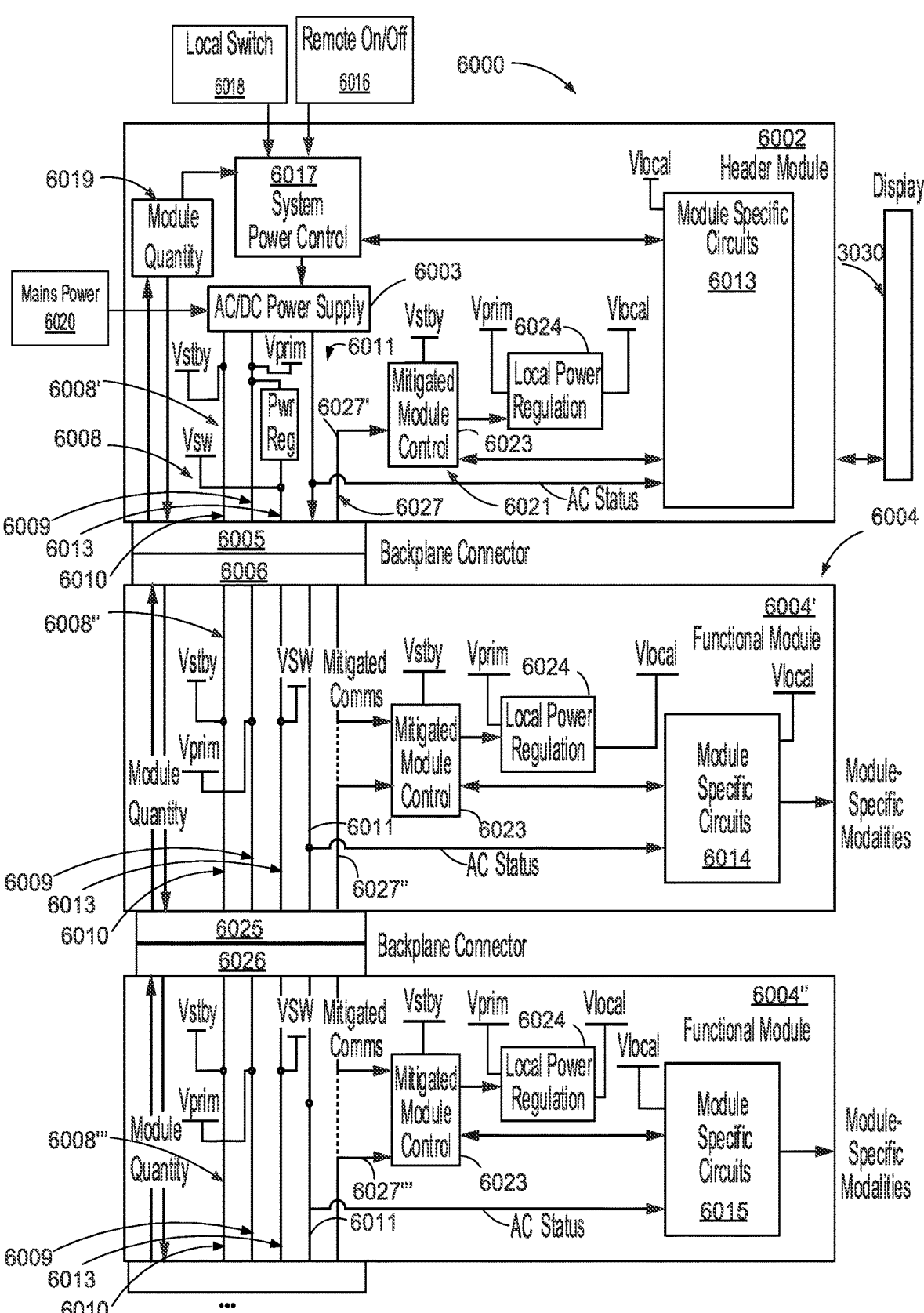
FIG. 11 is a schematic diagram of a modular energy system stack illustrating a power backplane, in accordance with at least one aspect of the present disclosure.

In various aspects, as illustrated in FIG. 11, a modular energy system 6000 that is similar in many respects to the modular energy systems 2000 (FIGS. 5-8), 3000 (FIGS. 9-10). For the sake of brevity, various details of the modular energy system 6000, which are similar to the modular energy system 2000 and/or the modular energy system 3000, are not repeated herein.

The modular energy system 6000 comprises a header module 6002 and an "N" number of surgical modules 6004, where "N" is an integer greater than or equal to one. In various examples, the modular energy system 6000 includes a UI module such as, for example, the UI module 3030 and/or a communication module such as, for example, the communication module 3032. Furthermore, pass-through hub connectors couple individual modules to one another in a stack configuration. In the example of FIG. 11, the header module 6002 is coupled to a surgical module 6004 via pass-through hub connectors 6005, 6006.

The modular energy system 6000 comprises an example power architecture that consists of a single AC/DC power supply 6003 that provides power to all the surgical modules in the stack. The AC/DC power supply 6003 is housed in the header module 6002, and utilizes a power backplane 6008 to distribute power to each module in the stack. The example of FIG. 11 demonstrates three separate power domains on the power backplane 6008: a primary power domain 6009, a standby power domain 6010, and an Ethernet switch power domain 6013.

In the example illustrated in FIG. 11, the power backplane 6008 extends from the header module 6002 through a number of intermediate modules 6004 to a most bottom, or farthest, module in the stack. In various aspects, the power backplane 6008 is configured to deliver power to a surgical module 6004 through one or more other surgical modules 6004 that are ahead of it in the stack. The surgical module 6004 receiving power from the header module 6002 can be coupled to a surgical instrument or tool configured to deliver therapeutic energy to a patient.

The primary power domain 6009 is the primary power source for the functional module-specific circuits 6013, 6014, 6015 of the modules 6002, 6004. It consists of a single voltage rail that is provided to every module. In at least one example, a nominal voltage of 60V can be selected to be higher than the local rails needed by any module, so that the modules can exclusively implement buck regulation, which is generally more efficient than boost regulation.

In various aspects, the primary power domain 6009 is controlled by the header module 6002. In certain instances, as illustrated in FIG. 11, a local power switch 6018 is positioned on the header module 6002. In certain instances, a remote on/off interface 6016 can be configured to control a system power control 6017 on the header module 6002, for example. In at least one example, the remote on/off interface 6016 is configured to transmit pulsed discrete commands (separate commands for On and Off) and a power status telemetry signal. In various instances, the primary power domain 6009 is configured to distribute power to all the modules in the stack configuration following a user-initiated power-up.

In various aspects, as illustrated in FIG. 11, the modules of the modular energy system 6000 can be communicably coupled to the header module 6002 and/or to each other via a communication (Serial bus/Ethernet) interface 6040 such that data or other information is shared by and between the modules of which the modular energy system is constructed. An Ethernet switch domain 6013 can be derived from the primary power domain 6009, for example. The Ethernet switch power domain 6013 is segregated into a separate power domain, which is configured to power Ethernet switches within each of the modules in the stack configuration, so that the primary communications interface 6040 will remain alive when local power to a module is removed. In at least one example, the primary communication interface 6040 comprises a 1000BASE-T Ethernet network, where each module represents a node on the network, and each module downstream from the header module 6002 contains a 3-port Ethernet switch for routing traffic to the local module or passing the data up or downstream as appropriate.

Furthermore, in certain examples, the modular energy system 6000 includes secondary, low speed, communication interface between modules for critical, power related functions including module power sequencing and module power status. The secondary communications interface can, for example, be a multi-drop Local Interconnect Network (LIN), where the header module is the master and all downstream modules are slaves.

In various aspects, as illustrated in FIG. 11, a standby power domain 6010 is a separate output from the AC/DC power supply 6003 that is always live when the supply is connected to mains power 6020. The standby power domain 6010 is used by all the modules in the system to power circuitry for a mitigated communications interface, and to control the local power to each module. Further, the standby power domain 6010 is configured to provide power to circuitry that is critical in a standby mode such as, for example, on/off command detection, status LEDs, secondary communication bus, etc.

In various aspects, as illustrated in FIG. 11, the individual surgical modules 6004 lack independent power supplies and, as such, rely on the header module 6002 to supply power in the stack configuration. Only the header module 6002 is directly connected to the mains power 6020. The surgical modules 6004 lack direct connections to the mains power 6020, and can receive power only in the stack configuration. This arrangement improves the safety of the individual surgical modules 6004, and reduces the overall footprint of the modular energy system 6000. This arrangement further reduces the number of cords required for proper operation of the modular energy system 6000, which can reduce clutter and footprint in the operating room.

Accordingly, a surgical instrument connected to surgical modules 6004 of a modular energy system 6000, in the stack configuration, receives therapeutic energy for tissue treatment that is generated by the surgical module 6004 from power delivered to the surgical module 6004 from the AC/DC power supply 6003 of the header module 6002.

In at least one example, while a header module 6002 is assembled in a stack configuration with a first surgical module 6004', energy can flow from the AC/DC power supply 6003 to the first surgical module 6004'. Further, while a header module 6002 is assembled in a stack configuration with a first surgical module 6004' (connected to the header module 6002) and a second surgical module 6004" (connected to the first surgical module 6004'), energy can flow from the AC/DC power supply 6003 to the second surgical module 6004" through the first surgical module 6004'.

The energy generated by the AC/DC power supply 6003 of the header module 6002 is transmitted through a segmented power backplane 6008 defined through the modular energy system 6000. In the example of FIG. 11, the header module 6002 houses a power backplane segment 6008', the first surgical module 6004' houses a power backplane segment 6008", and the second surgical module 6004" houses a power backplane segment 6008". The power backplane segment 6008' is detachably coupled to the power backplane segment 6008" in the stack configuration. Further, the power backplane 6008" is detachably coupled to the power backplane segment 6008"' in the stack configuration. Accordingly, energy flows from the AC/DC power supply 6003 to the power backplane segment 6008', then to the power backplane segment 6008", and then to the power backplane segment 6008"'.

In the example of FIG. 11, the power backplane segment 6008' is detachably connected to the power backplane segment 6008" via pass-through hub connectors 6005, 6006 in the stack configuration. Further, the power backplane segment 6008" is detachably connected to the power backplane segment 6008"' via pass-through hub connectors 6025, 6056 in the stack configuration. In certain instances, removing a surgical module from the stack configuration severs its connection to the power supply 6003. For example, separating the second surgical module 6004" from the first surgical module 6004' disconnects the power backplane segment 6008"' from the power backplane segment 6008". However, the connection between the power backplane segment 6008" and the power backplane segment 6008"' remains intact as long as the header module 6002 and the first surgical module 6004' remain in the stack configuration. Accordingly, energy can still flow to the first surgical module 6004' after disconnecting the second surgical module 6004" through the connection between the header module 6002 and the first surgical module 6004'. Separating connected modules can be achieved, in certain instances, by simply pulling the surgical modules 6004 apart.

In the example of FIG. 11, each of the modules 6002, 6004 includes a mitigated module control 6023. The mitigated module controls 6023 are coupled to corresponding local power regulation modules 6024 that are configured to regulate power based on input from the mitigated module controls 6023. In certain aspects, the mitigated module controls 6023 allow the header module 6002 to independently control the local power regulation modules 6024.

The modular energy system 6000 further includes a mitigated communications interface 6021 that includes a segmented communication backplane 6027 extending between the mitigated module controls 6023. The segmented communication backplane 6027 is similar in many respects to the segmented power backplane 6008. Mitigated Communication between the mitigated module controls 6023 of the header module 6002 and the surgical modules 6004 can be achieved through the segmented communication backplane 6027 defined through the modular energy system 6000. In the example of FIG. 11, the header module 6002 houses a communication backplane segment 6027', the first surgical module 6004' houses a communication backplane segment 6027", and the second surgical module 6004" houses a communication backplane segment 6027'". The communication backplane segment 6027' is detachably coupled to the communication backplane segment 6027" in the stack configuration via the pass-through hub connectors 6005, 6006. Further, the communication backplane 6027" is detachably coupled to the communication backplane segment 6027" in the stack configuration via the pass-through hub connectors 6025, 6026.

Although the example of FIG. 11 depicts a modular energy system 6000 includes a header module 6002 and two surgical modules 6004' 6004", this is not limiting. Modular energy systems with more or less surgical modules are contemplated by the present disclosure. In some aspects, the modular energy system 6000 includes other modules such as, for example, a communications module. In some aspects, the header module 6502 supports a display screen such as, for example, the display 2006 (FIG. 6A) that renders a GUI such as, for example, the GUI 2008 for relaying information regarding the modules connected to the header module 6002. The GUI 2008 of the display screen 2006 can provide a consolidated point of control all of the modules making up the particular configuration of a modular energy system.

Figure 12:
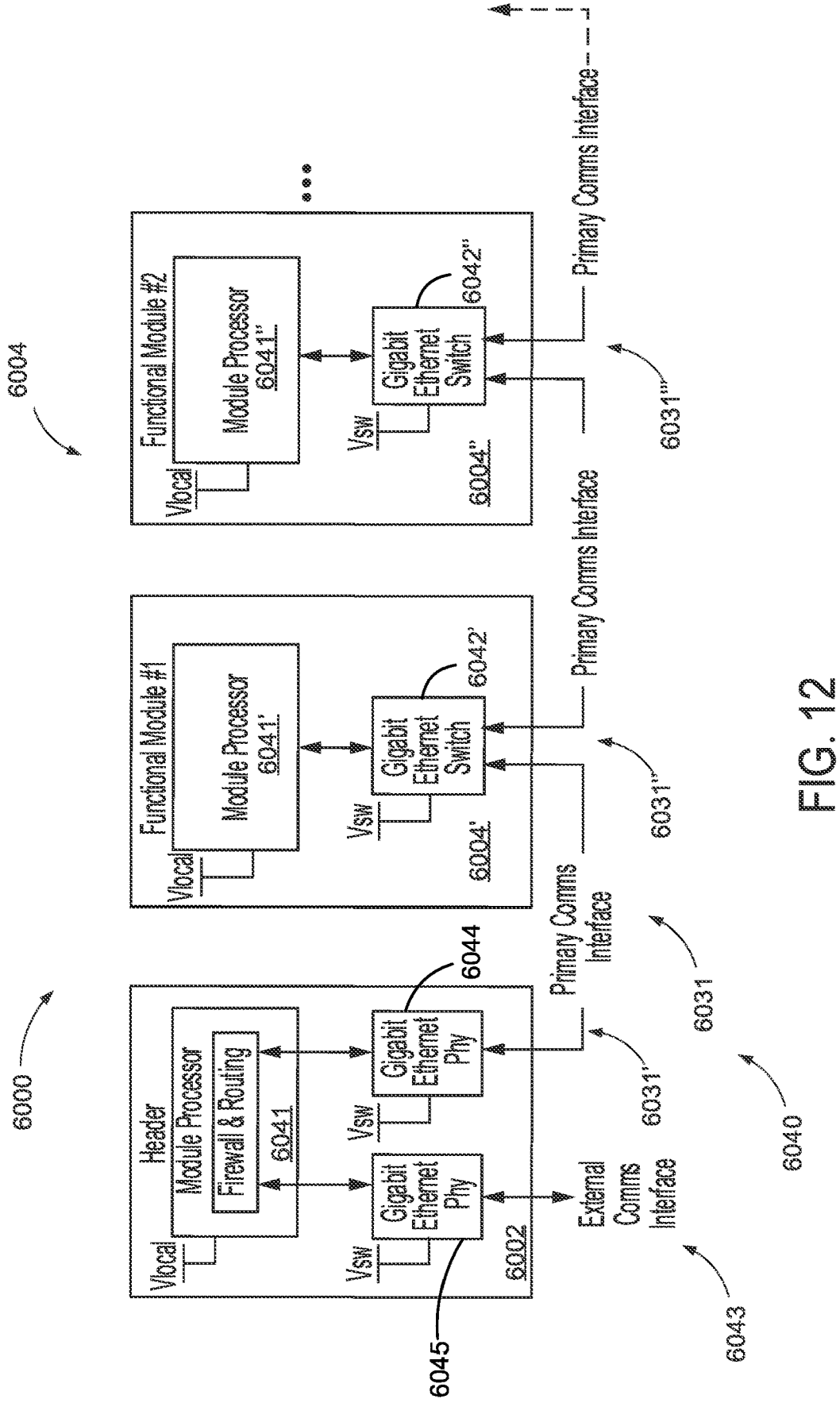
FIG. 12 is a schematic diagram of a modular energy system, in accordance with at least one aspect of the present disclosure.

FIG. 12 depicts a simplified schematic diagram of the modular energy system 6000, which illustrates a primary communications interface 6040 between the header module 6002 and the surgical modules 6004. The primary communications interface 6040 communicably connects module processors 6041, 6041', 6041" of the header module 6002 and the surgical modules 6004. Commands generated by the module processor 6041 of the header module are transmitted downstream to a desired functional surgical module via the primary communications interface 6040. In certain instances, the primary communications interface 6040 is configured to establish a two-way communication pathway between neighboring modules. In other instances, the primary communications interface 6040 is configured to establish a one-way communication pathway between neighboring modules.

Furthermore, the primary communications interface 6040 includes a segmented communication backplane 6031, which is similar in many respects to the segmented power backplane 6008. Communication between the header module 6002 and the surgical modules 6004 can be achieved through the segmented communication backplane 6031 defined through the modular energy system 6000. In the example of FIG. 12, the header module 6002 houses a communication backplane segment 6031', the first surgical module 6004' houses a communication backplane segment 6031", and the second surgical module 6004" houses a communication backplane segment 6031'". The communication backplane segment 6031' is detachably coupled to the communication backplane segment 6031" in the stack configuration via the pass-through hub connectors 6005, 6006. Further, the communication backplane 6031" is detachably coupled to the communication backplane segment 6031" in the stack configuration via the pass-through hub connectors 6025, 6026.

Figure 16:
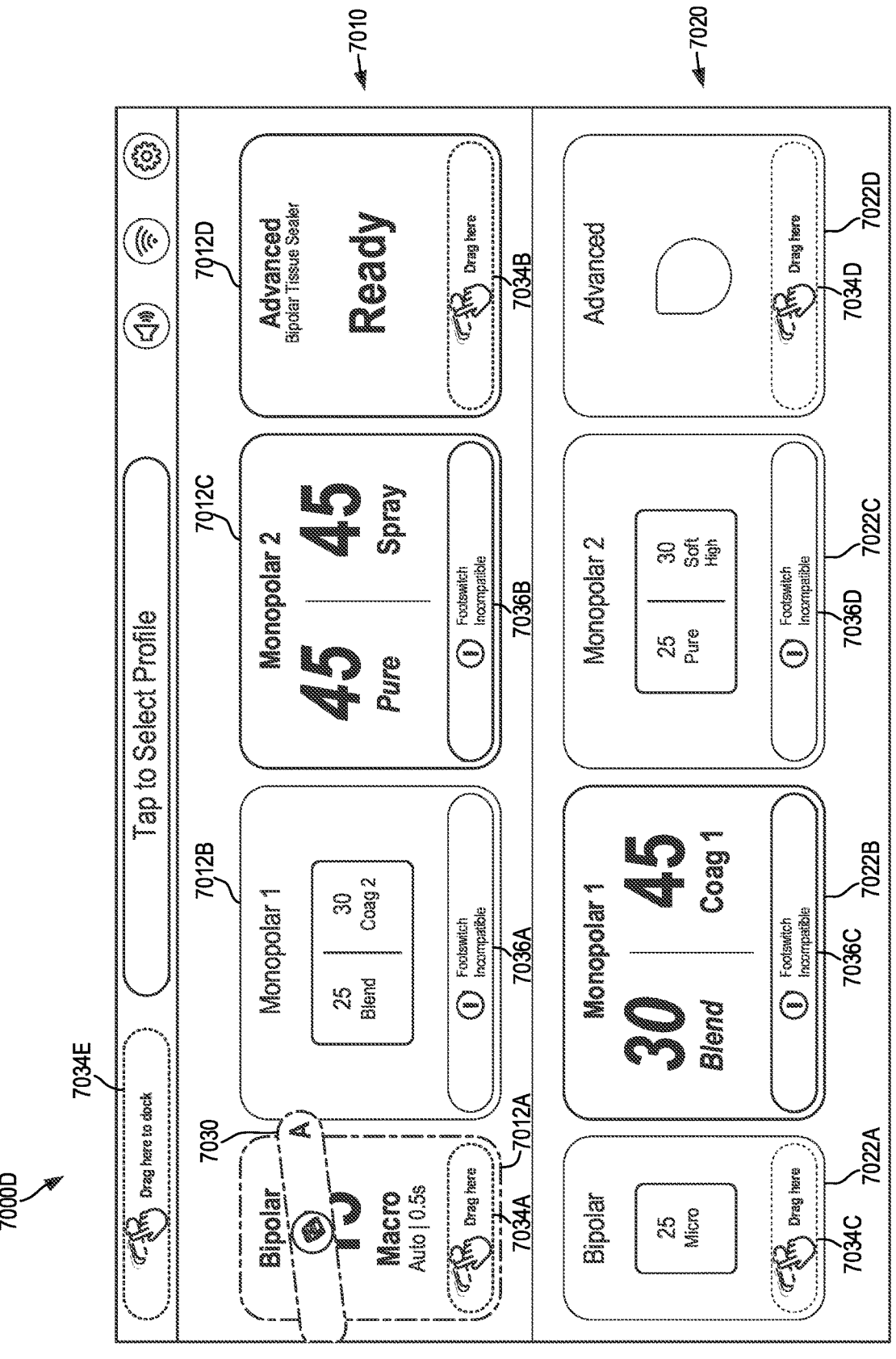
Figure 17:
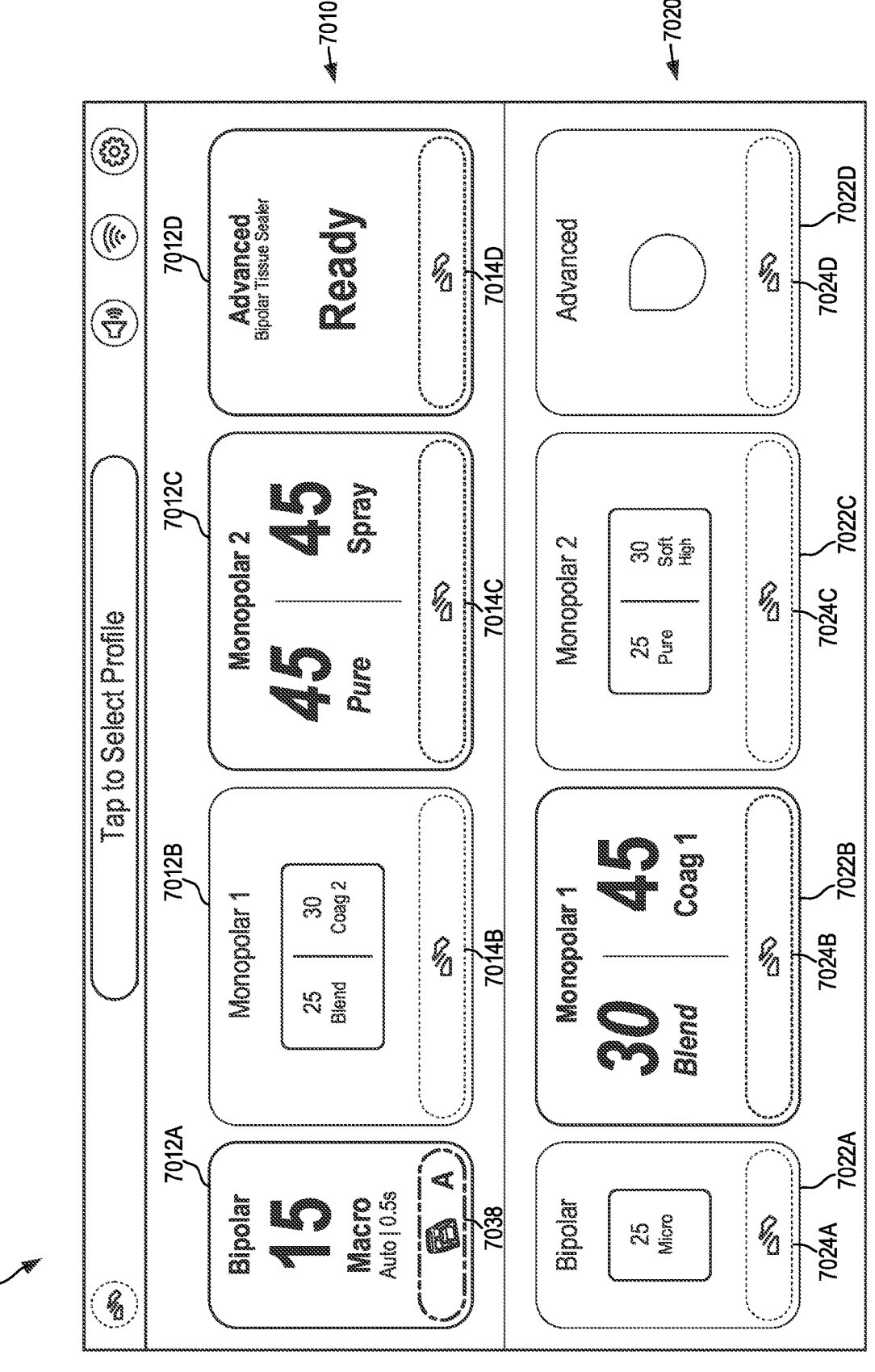

In at least one example, as illustrated in FIG. 12, the primary communications interface 6040 is implemented using the DDS framework running on a Gigabit Ethernet interface. The module processors 6041, 6041', 6041" are connected to Gigabit Ethernet Phy 6044, and Gigabit Ethernet Switches 6042', 6042". In the example of FIG. 16, the segmented communication backplane 6031 connects the Gigabit Ethernet Phy 6044 and the Gigabit Ethernet Switches 6042 of the neighboring modules.

In various aspects, as illustrated in FIG. 12, the header module 6002 includes a separate Gigabit Ethernet Phy 6045 for an external communications interface 6043 with the processor module 6041 of the header module 6002. In at least one example, the processor module 6041 of the header module 6002 handles firewalls and information routing.

Referring to FIG. 11, the AC/DC power supply 6003 may provide an AC Status signal 6011 that indicates a loss of AC power supplied by the AC/DC power supply 6003. The AC status signal 6011 can be provided to all the modules of the modular energy system 6000 via the segmented power backplane 6008 to allow each module as much time as possible for a graceful shutdown, before primary output power is lost. The AC status signal 6011 is received by the module specific circuits 6013, 6014, 6015, for example. In various examples, the system power control 6017 can be configured to detect AC power loss. In at least one example, the AC power loss is detected via one or more suitable sensors.

Referring to FIGS. 11 and 12, to ensure that a local power failure in one of the modules of the modular energy system 6000 does not disable the entire power bus, the primary power input to all modules can be fused or a similar method of current limiting can be used (e-fuse, circuit breaker, etc.). Further, Ethernet switch power is segregated into a separate power domain 6013 so that the primary communications interface 6040 remains alive when local power to a module is removed. In other words, primary power can be removed and/or diverted from a surgical module without losing its ability to communicate with other surgical modules 6004 and/or the header module 6002.

Footswitch Assignment Using a Graphical User Interface

Having described a general implementation of modular energy systems 2000, 3000, 6000 and graphical user interface (GUI) 2008, the disclosure now turns to describe various implementations of other modular energy systems and GUIs. The other modular energy systems are substantially similar to the modular energy system 2000, the modular energy system 3000, and/or the modular energy system 6000. Likewise, the other GUIs are substantially similar to GUI 2008. For the sake of brevity, various details of the other modular energy systems and GUIs described in the following sections are not repeated herein. Any aspect of the other modular energy systems and GUIs described below can be brought into the modular energy system 2000, the modular energy system 3000, the modular energy system 6000, and the GUI 2008.

As described above, modular energy systems can include one or multiple energy modules each configured to generate one or multiple energy modalities for driving electrosurgical and/or ultrasonic surgical instruments connected thereto. For example, referring again to FIG. 7, the modular energy system 2000 is illustrated as having two energy modules (energy modules 2004a and 2004b), with each energy module having a port assembly (port assembly 2012a or 2012b), and with each port assembly having a number of different ports configured to deliver different energy modalities to corresponding surgical instruments that are connectable thereto. In other aspects, modular energy system 2000 can include more than two energy modules, with each energy module each having a port assembly with different ports.

As also described above, modular energy systems can include a variety of accessories connectable to the modules for controlling functions thereof. These accessories can include footswitches configured to control the activation or function of the energy modalities generated by the modules. For example, referring again to FIG. 5, footswitches used with modular energy systems can include single-pedal footswitches (e.g., single-pedal footswitch 2032) and dual-pedal footswitches (e.g., dual-pedal footswitch 2034). In some aspects, each footswitch is configured to control only one port of the modular energy system at a time. In other aspects, the footswitches can be communicatively coupled to the modular energy system via a wired connection. In yet other aspects, footswitches can be coupled to the modular energy system via a wireless connection. Any number and combination of the same and/or different types footswitches can be connected to a single modular energy system to control the various ports.

Accordingly, not only is there a variety of different energy module and port configurations that can be used to implement the modular energy systems described herein, but also a variety of different footswitch configurations that can be used to control the energy modalities associated with the ports. Given the various combinations of energy modules, energy modalities, ports, and footswitches that may be implemented for a particular modular energy system, there exists a need for devices, systems, and methods for easily assigning a footswitch to control a particular port of a modular energy system. Additionally, because some footswitches may be wirelessly connected to modular energy systems, there exists a need for devices, systems, and methods for both wirelessly pairing a footswitch to a modular energy system and assigning the footswitch to control a particular port thereof. The present disclosure provides devices, systems, and methods for assigning footswitches to control particular ports of a modular energy system using a graphical user interface (GUI). The present disclosure also provides devices, systems, and methods for wirelessly pairing footswitches to a modular energy system and assigning the footswitches to control particular ports thereof using a GUI.

FIGS. 13-17 depict an illustrative sequence of GUI screens 7000A-E (collectively representing GUI 7000) for assigning footswitches to particular ports of a modular energy system, according to several non-limiting aspects of the present disclosure. GUI 7000 can be rendered by a display screen of a modular energy system. For example, similar to the GUI 2008, GUI 7000 can be rendered by display screen 2006 of the modular energy system 2000 referenced above with respect to FIGS. 5-8. Although FIGS. 13-17 depict a GUI rendered by a modular energy system having a specific configuration of footswitches, modules, and ports, those of ordinary skill in the art will appreciate that the aspects disclosed below with respect to FIGS. 13-17 can be applied to modular energy systems having a variety of different footswitch, module, and port configurations.

Figure 13:
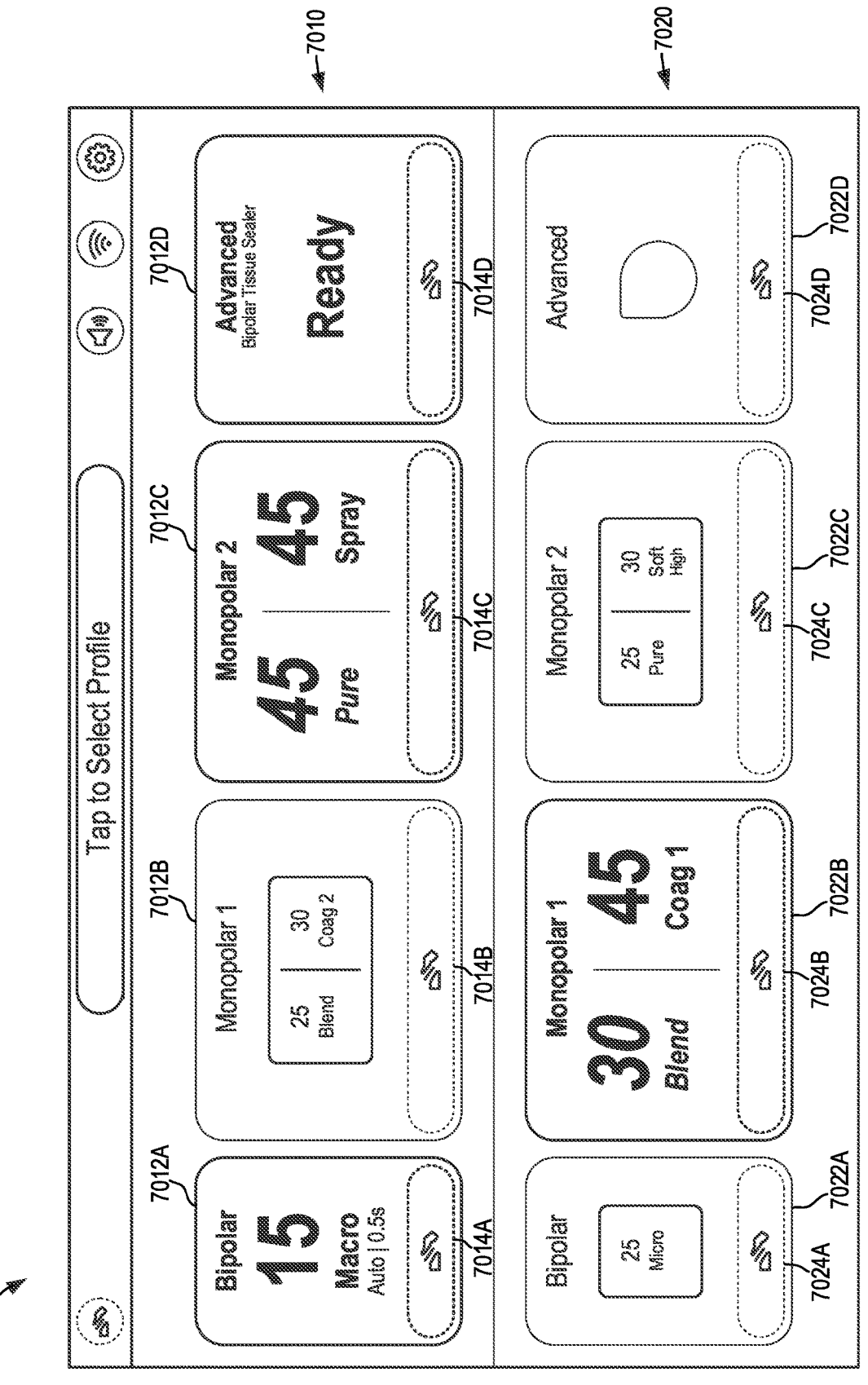
FIGS. 13-17 are illustrative graphical user interface screens for assigning footswitches to control specific ports of a modular energy system, in accordance with several aspects of the present disclosure.

Referring now to FIG. 13, GUI screen 7000A is illustrated displaying data and controls related to an illustrative modular energy system configured with a first energy module and a second energy module (e.g., similar modular energy system 2000 of FIG. 7, which includes a first energy module

2004a and a second energy module 2004b). Specifically, GUI screen 7000A includes a first portion 7010 corresponding to the first energy module and a second portion 7020 corresponding to the second energy module. The first portion 7010 of GUI screen 7000A includes a first widget 7012A, a second widget 7012B, a third widget 7012C, and a fourth widget 7012D each displaying data and controls that respectively correspond to a bipolar port, a first monopolar port, a second monopolar port, and a combination energy port of the first energy module (e.g., bipolar port 2014, first monopolar port 2016a, second monopolar port 2016b, and combination energy port 2020 of energy module 2004 of FIG. 6A). Likewise, the second portion 7020 of GUI screen 7000A includes a first widget 7022A, a second widget 7022B, a third widget 7022C, and a fourth widget 7022D each displaying data and controls that respectively correspond to a bipolar port, a first monopolar port, a second monopolar port, and a combination energy port of the second energy module. Each widget 7012A-D, 7022A-D of GUI screen 7000A includes an icon 7014A-D, 7024A-D indicating that the corresponding port is available to be controlled by a footswitch but no footswitch has been assigned to that port. As noted above, as different and/or additional modules are connected to the modular energy system stack, the GUI 7000 can adjust to accommodate the different and/or additional controls for the updated modular energy system configuration.

The modular energy system, based on detecting that a footswitch has been connected to thereto, can cause GUI 7000 to display one or more GUI elements indicating that the connected footswitch is available to be assigned to one of the ports. For example, referring now to FIG. 14, GUI screen 7000B is illustrated displaying an object 7030 based on the modular energy system detecting a connected footswitch. The connected footswitch may be a wired footswitch or a wireless footswitch. Thus, in one aspect, detecting a connected footswitch can include detecting that the footswitch has been plugged into one of the modules of the modular energy system via a wired connection. In another aspect, detecting a connected footswitch can include detecting that the footswitch has been wirelessly paired with the modular energy system.

In addition to or in lieu of the above, the connected footswitch may be a single-pedal footswitch or a dual-pedal footswitch (e.g., single-pedal footswitch 2032 or dual-pedal footswitch 2034 of FIG. 5). Thus, in one aspect, the object 7030 can include an icon that indicates whether the connected footswitch is a single-pedal footswitch or a dual-pedal foot switch. For example, in the non-limiting aspect of FIG. 14, the object 7030 includes an icon representing a single-pedal footswitch (indicating that a single-pedal footswitch has been connected). If instead a dual-pedal footswitch had been connected, the object 7030 may include an icon representing the dual-pedal footswitch.

Figure 14:
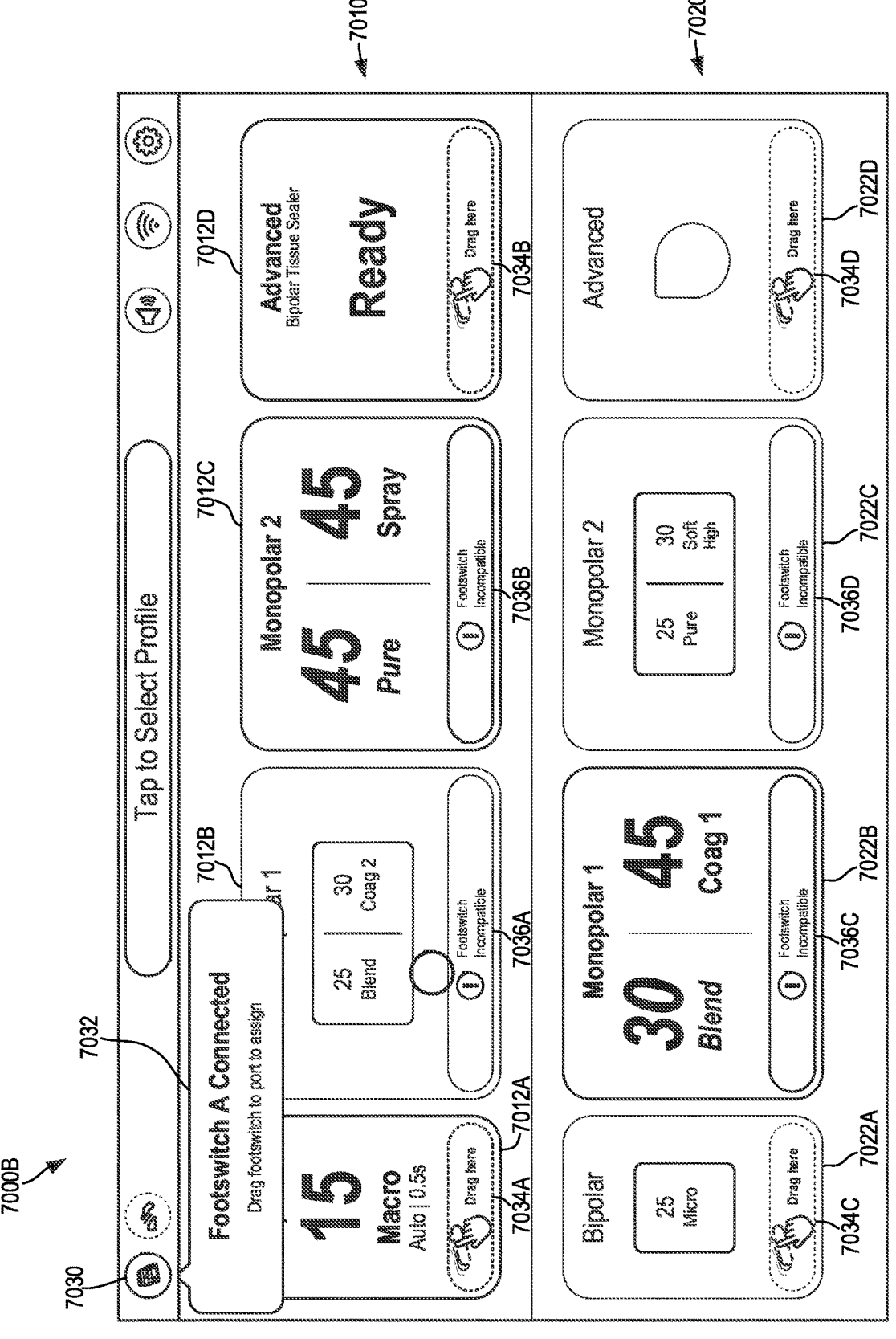
Figure 15:
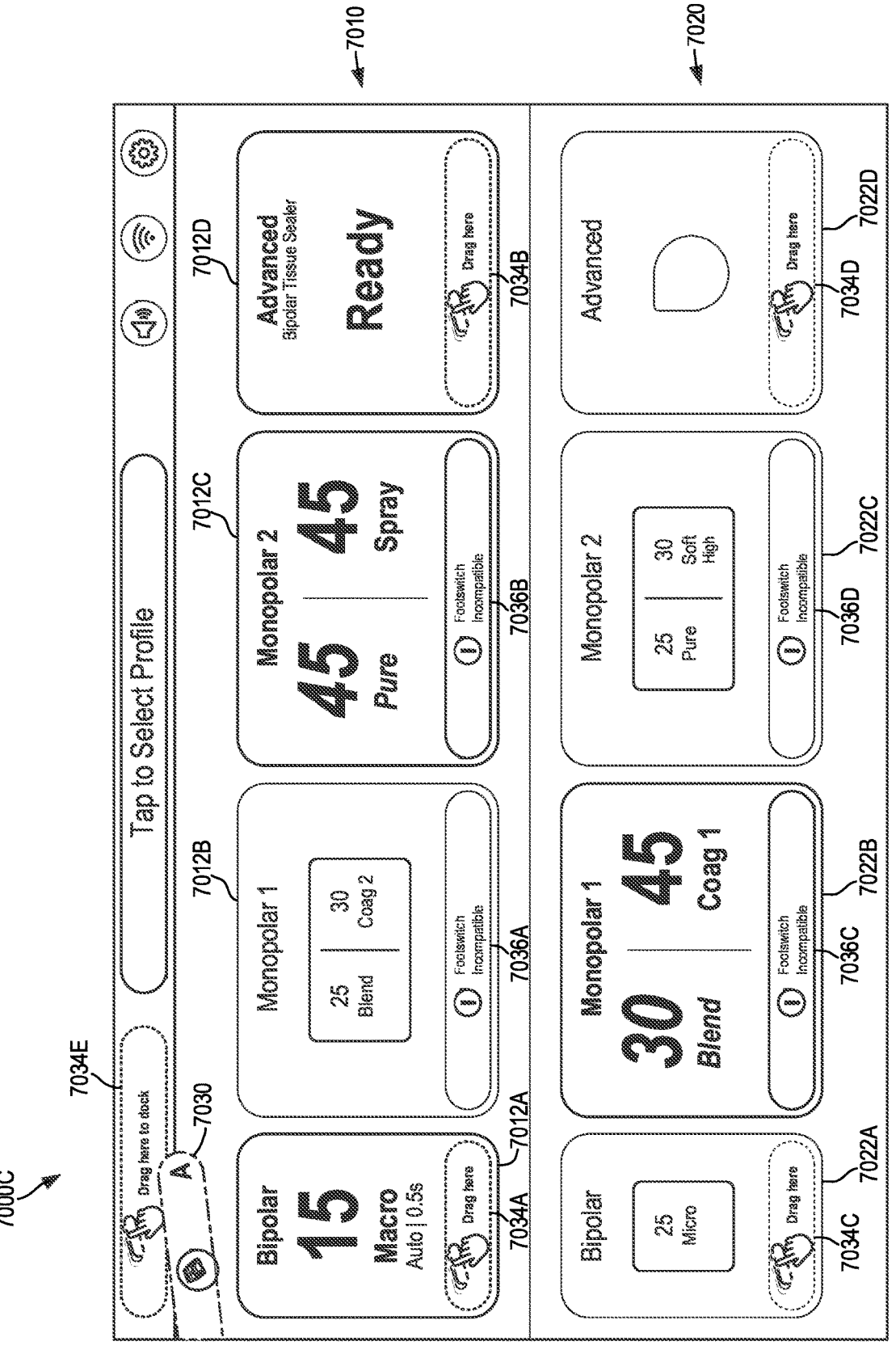

Still referring to FIG. 14, based on detecting a connected footswitch, the modular energy system can cause GUI screen 7000B to display a help balloon 7032. The help balloon 7032 can include a notification identifying the connected footswitch and/or instructions for assigning the connected footswitch to an available port. For example, the help balloon 7032 includes text reciting "Footswitch A Connected" and "Drag footswitch to port to assign." Thus, a user viewing GUI screen 7000B and help balloon 7032 is notified that Footswitch A is connected and can be assigned to a particular port by dragging the object 7030 to one of the available widgets (e.g., 7012A, 7012D, 7022A, 7022D).

In various aspects, based on detecting a connected footswitch, the GUI 7000 can display icons and/or text identifying the ports to which the footswitch can be assigned. For example, referring still to FIG. 14, the GUI screen 7000B is illustrated displaying icons 7034A-D along with the text "Drag here" inside widgets 7012A, 7012D, 7022A, 7022D indicating that the object 7030 can be dragged to any of those widget to assign the footswitch. In one aspect, the modular energy system may determine the ports to which the footswitch can be assigned based on whether the connected footswitch is a single-pedal footswitch or a dual-pedal footswitch. For example, in the non-limiting aspect of FIG. 14, only the bipolar and combination energy ports of the modular energy system are configured to support a single-pedal footswitch. Accordingly, the widgets 7012A, 7012D, 7022A, and 7022D include the icons 7034A-D indicting that the footswitch can be assigned to one of those ports. Conversely, widgets 7012B, 7012C, 7022B, and 7022C include text 7036A-D indicating that the connected footswitch is incompatible with corresponding the monopolar ports and therefore cannot be assigned thereto.

A user of the modular energy system can interact with the GUI screen 7000B to pair the connected footswitch with one of the available ports. For example, following the instructions provided by the help balloon 7032 and/or icons 7034A-D, the user can press and drag the object 7030 away from its original position. Transitioning from GUI screen 7000B to GUI screen 7000C of FIG. 15, pressing and dragging the object 7030 will cause the object to move about the GUI screen 7000C thereby allowing the user to drag the object 7030 to an available port (i.e., to one of the widgets 7012A, 7012D, 7022A, or 7022D displaying the "Drag here" icon 7034A-D). Pressing and dragging object 7030 can also cause GUI screen 7000C to display an icon 7034E including text reciting "Drag here to dock." Rather than dragging the object 7030 to one of the available ports (i.e., widgets), the user can drag the object 7030 back to its original position and release the object 7030 to return to GUI screen 7000B. As a result of this action, the footswitch will remain unassigned. In some aspects, if the user releases the object 7030 without dragging to any of the widgets having icons 7034A-E, the footswitch will remain unassigned and the GUI 7000 will return to GUI screen 7000B.

Transitioning from GUI screen 7000C to GUI screen 7000D of FIG. 16, as the result of a dragging motion performed by the user, the object 7030 is depicted hovering over widget 7012A. In some aspects, dragging the objet 7030 over one of the available/compatible widgets will cause the widget to become highlighted and/or have a dashed border. For example, GUI screen 7000D shows widget 7012A with a highlighted/dashed border based on a user dragging object 7030 thereover. The highlighted/dashed border can indicate that the widget 7012A (and the corresponding bipolar port) is compatible with the footswitch and/or that another footswitch has not already been assigned to widget 7012A.

Once the user has dragged the object 7030 over the desired widget, the user can release the object 7030 to cause the modular energy system to assign the footswitch to the port associated with the widget. Transitioning from GUI screen 7000D to GUI screen 7000E of FIG. 17, as the result of the user dragging and releasing object 7030 while it is positioned over widget 7012A, an icon 7038 is depicted inside of widget 7012A. The icon 7038 includes a depiction of a single-pedal footswitch and the text "A." Thus, icon 7038 indicates that Footswitch A, a single-pedal footswitch, has been assigned to the bipolar port of the first energy module of the modular energy system.

Returning to GUI screen 7000B of FIG. 14, in some aspects, a user may not wish to immediately assign a footswitch once it has been connected. For example, the user may want to adjust another setting of the modular energy system using the GUI 7000 before assigning the footswitch. Thus, the user may wish to remove the help balloon 7032 from the screen. In one aspect, the help balloon 7032 can be removed from GUI screen 7000B by tapping anywhere on the screen. In another aspect, the help balloon 7032 can be removed from GUI screen 7000B by tapping anywhere on the screen except on the help balloon 7032 and/or the object 7030. In another aspect, the help balloon 7032 is automatically removed from the GUI screen 7000B after a predetermined time period.

Still referring to GUI screen 7000B of FIG. 14, multiple footswitches may be connected to the modular energy system. In some aspects, multiple footswitches may be connected to the modular energy system with at least some of the connected footswitches not being assigned to a port. For example, GUI screen 7000B indicates that Footswitch A is connected and unassigned. Prior to assigning Footswitch A to a particular port, another footswitch may be connected to the modular energy system. If a second footswitch (e.g., Footswitch B) is connected, then GUI 7000 may update to display another draggable object for the second footswitch (not shown in FIG. 14), similar to the object 7030 for Footswitch A. The draggable object for the second footswitch can include an icon representing a single-pedal or a dual-pedal footswitch depending on the type of footswitch that is connected. GUI 7000 may also update to instead display a help balloon indicating that the second footswitch has been connected (e.g., with text reciting "Footswitch B Connected"), similar to the help balloon 7032 for Footswitch A. Additional draggable objects can be generated for additional connected and unassigned footswitches (e.g., Footswitch C, Footswitch D, etc.). Thus, GUI 7000 can display multiple draggable objects similar to 7030, thereby allowing the user to select and assign one of multiple connected footswitches to a particular port of the modular energy system.

As mentioned above, various footswitches may be wirelessly connected to the modular energy systems described herein. In order to connect a wireless footswitch to a modular energy system, the footswitch may first need to be detected by the modular energy system and then paired to the modular energy system based on user input (e.g., via a user interacting with a GUI of the modular energy system). Following pairing, the user is able to assign the wireless footswitch to a particular port as described above. However, it may be desirable to both pair a wireless footswitch to the modular energy and assign the footswitch to a particular port based on a single drag and drop action.

The GUI 7000 can display a sequence of screens similar to the GUI screens 7000A-E of FIGS. 13-17 that allow a user to both wirelessly pair a footswitch to the modular energy system and assign the footswitch to a port using a single action. For example, starting at GUI screen 7000A of FIG. 13 and transitioning to GUI screen 7000B of FIG. 14, GUI 7000 can display an object 7030 and or a help balloon 7032 indicating that a wireless footswitch has been detected by the modular energy system and is available. In this aspect, help balloon 7032 may display text identifying the detected wireless footswitch (e.g., "Footswitch A Detected"). The help balloon 7032 may also display text instructing the user how to pair and assign the wireless footswitch (e.g., "Drag footswitch to port to pair and assign"). Similar to the above, the GUI 7000 can display icons 7034A-D indicating which ports are compatible with the detected footswitch. Further, GUI 7000 can implement screens similar to GUI screens 7000C-E described above with respect to FIGS. 15-17 allowing the user to perform a single drag-and-drop action that causes the detected footswitch to be paired to the modular energy system.

FIG. 18 illustrates a method 5000 for assigning a footswitch to control a port of a modular energy system, according to several non-limiting aspects of this disclosure. The method 5000 may be practiced by any combination of the surgical systems, modular energy systems, energy modules, header modules, footswitches, ports, surgical instruments, any of the components thereof, and any other devices and systems disclosed herein. For example, the method 5000 may be practiced by a modular energy system including an energy module and a display screen configured to render a graphical user interface (GUI). The energy module can include ports configured to deliver energy modalities to surgical instruments coupled thereto.

In accordance with the method 5000, the GUI can display 5002 a plurality of widgets corresponding to the ports. The modular energy system can detect 5004 that a footswitch is available to be assigned to one of the ports. Based on the detection of the footswitch, the GUI can display 5006 an object indicating that the footswitch is available to be assigned to one of the ports. The modular energy system can identify 5008 one or more of the ports that are available to be controlled by the footswitch. Further, the GUI can display 5010 an icon in the widgets corresponding to the one or more ports identified as available to be controlled by the footswitch. In some aspects, the icon can indicate that the port is available to be controlled by the footswitch. Based on a user interacting with the GUI to drag and drop the object into one of the widgets, the modular energy system can assign 5012 the footswitch to one of the ports.

In one aspect of the method 5000, detecting 5004 that a footswitch is available to be assigned to one of the ports can include detecting that the footswitch is connected to the modular energy system via a wired connection and/or detecting that the footswitch is wirelessly paired with the modular energy system. In another aspect of the method 5000, detecting 5004 that a footswitch is available to be assigned to one of the ports can include detecting that the footswitch is available to be wirelessly paired with the modular energy system. In this aspect, the method 5000 can further include wirelessly pairing the footswitch with the modular energy system based on the user interacting with the GUI to drag and drop the object into one of the widgets having the icon. Thus, based on the same drag and drop interaction with the GUI by the user, the footswitch is both assigned to one of the ports and wirelessly paired with the modular energy system.

In one aspect of the method 5000, detecting 5004 that a footswitch is available to be assigned to one of the ports can include determining that the footswitch is a single-pedal footswitch. Further, identifying 5008 one or more of the ports that are available to be controlled by the footswitch can include determining that one or more of the ports are compatible with a single-pedal footswitch. Yet further, in this aspect of the method 5000, the GUI can display a single-pedal footswitch icon in the object based on the modular energy system determining that the footswitch is a single-pedal footswitch.

In one aspect of the method 5000, detecting 5004 that a footswitch is available to be assigned to one of the ports can include determining that the footswitch is a dual-pedal footswitch. Further, identifying 5008 one or more of the ports that are available to be controlled by the footswitch can include determining that one or more of the ports are compatible with a dual-pedal footswitch. Yet further, in this aspect of the method 5000, the GUI can display a dual-pedal footswitch icon in the object based on the modular energy system determining that the footswitch is a dual-pedal footswitch.

In one aspect of the method 5000, identifying 5008 one or more of the ports that are available to be controlled by the footswitch can include determining that one or more of the ports do not already have a footswitch assigned thereto. In another aspect, the method 5000 can further include displaying, by the GUI, a footswitch icon in the widget corresponding to the port to which the footswitch is assigned.

In one aspect of the method 5000, the footswitch is a first footswitch and the object is a first object. The method 5000 can further include detecting, by the modular energy system, that a second footswitch is available to be assigned to one of the ports. Additionally, based on the detection of the second footswitch, the GUI can display a second object indicating that the second footswitch is available to be assigned to one of the ports. In another aspect, the method 5000 can further include displaying, by the GUI, help balloon including instructions to drag and drop the object to assign the footswitch (e.g., the first footswitch, the second footswitch) to one of the ports.

EXAMPLES

Various aspects of the devices, systems, and methods for assigning a footswitch to a port of a modular energy system described herein are set out in the following examples.

Example 1: A method of assigning a footswitch to control a port of a modular energy system, wherein the modular energy system comprises an energy module and a display screen configured to render a graphical user interface (GUI), and wherein the energy module comprises ports configured to deliver energy modalities to surgical instruments coupled thereto, the method comprising: displaying, by the GUI, a plurality of widgets corresponding to the ports; detecting, by the modular energy system, a footswitch is available to be assigned to one of the ports; displaying, by the GUI, an object indicating that the footswitch is available to be assigned to one of the ports based on the detection of the footswitch; identifying, by the modular energy system, one or more of the ports that are available to be controlled by the footswitch; displaying, by the GUI, an icon in the widgets corresponding to the one or more ports identified as available to be controlled by the footswitch, wherein the icon indicates that the port is available to be controlled by the footswitch; assigning, by the modular energy system, the footswitch to one of the ports based on a user interacting with the GUI to drag and drop the object into one of the widgets having the icon indicating that the port is available to be controlled by the footswitch.

Example 2: The method of Example 1, wherein detecting, by the modular energy system, that a footswitch is available to be assigned to one of the ports comprises at least one of: detecting that the footswitch is connected to the modular energy system via a wired connection; and detecting that the footswitch is wirelessly paired with the modular energy system.

Example 3: The method of any of Examples 1-2, wherein detecting, by the modular energy system, that a footswitch is available to be assigned to one of the ports comprises detecting that the footswitch is available to be wirelessly paired with the modular energy system; and wherein the method further comprises: wirelessly pairing the footswitch with the modular energy system based on the user interacting with the GUI to drag and drop the object into one of the widgets having the icon, wherein the footswitch is both assigned to one of the ports and wirelessly paired with the modular energy system based on the same drag and drop interaction with the GUI screen by the user.

Example 4: The method of any of Examples 1-3, wherein detecting, by the modular energy system, that a footswitch is available to be assigned to one of the ports comprises determining that the footswitch is a single-pedal footswitch; and wherein identifying, by the modular energy system, one or more of the ports that are available to be controlled by the footswitch comprises determining that one or more of the ports are compatible with a single-pedal footswitch.

Example 5: The method of any of Examples 1-4, further comprising: displaying, by the GUI, a single-pedal footswitch icon in the object based on the modular energy system determining that the footswitch is a single-pedal footswitch.

Example 6: The method of any of Examples 1-5, wherein detecting, by the modular energy system, that a footswitch is available to be assigned comprises determining that the footswitch is a dual-pedal footswitch; and wherein identifying, by the modular energy system, one or more of the ports that are available to be controlled by the footswitch comprises determining that one or more of the ports are compatible with a dual-pedal footswitch.

Example 7: The method of any of Examples 1-6, further comprising: displaying, by the GUI, an dual-pedal footswitch icon in the object based on the modular energy system determining that the footswitch is a dual-pedal footswitch.

Example 8: The method of any of Examples 1-7, wherein identifying, by the modular energy system, one or more of the ports that are available to be controlled by the footswitch comprises determining that one or more of the ports do not already have a footswitch assigned thereto.

Example 9: The method of any of Examples 1-8, further comprising: displaying, by the GUI, a footswitch icon in the widget corresponding to the port to which the footswitch is assigned.

Example 10: The method of any of Examples 1-9, wherein the footswitch is a first footswitch, wherein the object is a first object, the method further comprising: detecting, by the modular energy system, that a second footswitch is available to be assigned to one of the ports; displaying, by the GUI, a second object indicating that the second footswitch is available to be assigned to one of the ports based on the detection of the second footswitch.

Example 11: The method of any of Examples 1-10, further comprising: displaying, by the GUI, a help balloon including instructions to drag and drop the object to assign the footswitch to one of the ports.

Example 12: A modular energy system for use in a surgical environment, the modular energy system comprising: one or more energy modules, wherein each of the one or more energy modules comprises ports, and wherein each of the ports is configured to deliver an energy modality to a surgical instrument connected thereto; a footswitch configured to control the activation of at least one of the ports; a header module comprising a display screen, wherein the display screen is configured to render a graphical user interface (GUI), and wherein GUI is configured to: display a plurality of widgets, wherein each widget corresponds to one of the ports; display an object indicating that the footswitch is available to be assigned to one of the ports; display an icon in the widgets corresponding to the ports that are available to be controlled by the footswitch; and allow a user to drag and drop the object into one of the widgets having the icon, wherein dragging and dropping the object into one of the widgets having the icon causes the header module to assign the footswitch to the port corresponding to the widget.

Example 13: The system of Example 12, wherein the footswitch is configured to wirelessly pair with the header module, and wherein dragging and dropping the object into one of the widgets having the icon causes the header module to wirelessly pair with the footswitch.

Example 14: The system of any of Examples 12-13, wherein the footswitch is configured to communicatively connect to at least one of the header module and the one or more energy modules via a wired connection.

Example 15: The system of any of Examples 12-14, wherein the footswitch comprises a single-pedal footswitch or a dual-pedal footswitch.

Example 16: The system of any of Examples 12-15, wherein the GUI is configured to display the icon only in widgets corresponding to ports controllable by a single pedal footswitch if the footswitch comprises a single-pedal footswitch, and wherein the GUI is configured to display the icon only in widgets corresponding to ports controllable by a dual-pedal footswitch if the footswitch comprises a dual-pedal footswitch.

Example 17: The system of any of Examples 12-16, wherein the GUI is configured to display a single-pedal footswitch icon in the object if the footswitch comprises a single-pedal footswitch, and wherein the GUI is configured to display a dual-pedal footswitch icon in the object if the footswitch comprises a dual-pedal footswitch.

Example 18: The system of any of Examples 12-17, wherein dragging and dropping the object into one of the widgets having the icon causes the GUI to display a paired footswitch icon in the widget.

Example 19: The system of any of Examples 12-18, wherein the footswitch is a first footswitch, wherein the object is a first object, wherein the system further comprises a second footswitch, and wherein the GUI is further configured to simultaneously display the first object and a second object indicating that the second footswitch is available to be assigned to one of the ports.

Example 20: The system of any of Examples 12-19, wherein the GUI is further configured to display a help balloon including instructions to drag and drop the object to assign the footswitch to one of the ports.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A method for assigning a footswitch to control a port of a modular energy system, wherein the modular energy system comprises an energy module and a display screen configured to render a graphical user interface (GUI), and wherein the energy module comprises ports configured to deliver energy modalities to surgical instruments coupled thereto, the method comprising:

displaying, by the GUI, a plurality of widgets corresponding to the ports;

detecting, by the modular energy system, when a footswitch is available to be wirelessly connected to the modular energy system and is available to be assigned to one of the ports;

in response to detecting when the footswitch is available to be wirelessly connected to the modular energy system, displaying, by the GUI, an object representing the footswitch and indicating that the footswitch is available to be assigned to one of the ports;

identifying, by the modular energy system, one or more of the ports that are available to be controlled by the footswitch;

prior to any user interaction with the object, displaying, by the GUI, an icon in the widgets that correspond to the one or more ports identified as available to be controlled by the footswitch, wherein the icon indicates that the port is available to be controlled by the footswitch; and receiving a drag and drop input from a user interacting with the GUI, the drag and drop input including dragging and dropping the the object into one of the widgets displaying the icon indicating that the port is available to be controlled by the footswitch; and in response to the received drag and drop input, performing both of the following:

wirelessly pairing the footswitch with the modular energy system based on received drag and drop input, and assigning, by the modular energy system, the footswitch to one of the ports, the assignment being based on the received drag and drop input, such that the footswitch is both assigned to one of the ports and wirelessly paired with the modular energy system based on the same received drag and drop input.

2. The method of claim 1, wherein detecting, by the modular energy system, when the footswitch is available to be wirelessly connected to the modular energy system and is available to be assigned to one of the ports comprises determining that the footswitch is a single-pedal footswitch; and wherein identifying, by the modular energy system, one or more of the ports that are available to be controlled by the footswitch comprises determining that one or more of the ports are compatible with a single-pedal footswitch.

3. The method of claim 2, further comprising:

displaying, by the GUI, a single-pedal footswitch icon in the object based on the modular energy system determining that the footswitch is a single-pedal footswitch.

4. The method of claim 1, wherein detecting, by the modular energy system, when the footswitch is available to be wirelessly connected to the modular energy system and is available to be assigned comprises determining that the footswitch is a dual-pedal footswitch; and wherein identifying, by the modular energy system, one or more of the ports that are available to be controlled by the footswitch comprises determining that one or more of the ports are compatible with a dual-pedal footswitch.

5. The method of claim 4, further comprising:

displaying, by the GUI, a dual-pedal footswitch icon in the object based on the modular energy system determining that the footswitch is a dual-pedal footswitch.

6. The method of claim 1, wherein identifying, by the modular energy system, one or more of the ports that are available to be controlled by the footswitch comprises determining that one or more of the ports do not already have a footswitch assigned thereto.

7. The method of claim 1, further comprising:

displaying, by the GUI, a footswitch icon in the widget corresponding to the port to which the footswitch is assigned.

8. The method of claim 1, wherein the footswitch is a first footswitch, wherein the object is a first object, the method further comprising:

detecting, by the modular energy system, that a second footswitch is available to be assigned to one of the ports; and displaying, by the GUI, a second object indicating that the second footswitch is available to be assigned to one of the ports based on the detection of the second footswitch.

9. The method of claim 1, further comprising:

displaying, by the GUI, a help balloon including instructions to drag and drop the object to assign the footswitch to one of the ports.

10. A modular energy system for use in a surgical environment, the modular energy system comprising:

one or more energy modules, wherein each of the one or more energy modules comprises ports, wherein each of the ports is configured to deliver an energy modality to a surgical instrument connected thereto;

a footswitch configured to control the activation of at least one of the ports; and a header module comprising a display screen, wherein:

the footswitch is configured to wirelessly pair with the header module, the modular energy system is configured to:

detect when the footswitch is available to be wirelessly connected to the modular energy system and is available to be assigned one of the ports, and identify one or more of the ports that are available to be controlled by the footswitch; and the display screen is configured to:

render a graphical user interface (GUI)

display a plurality of widgets, wherein each widget corresponds to one of the ports;

in response to the modular energy system detecting when the footswitch is available to be wirelessly connected to the modular energy system and is available to be assigned to one of the ports, display an object indicating that the footswitch is available to be assigned to one of the ports;

prior to any user interaction with the object, display an icon in the widgets that correspond to the ports that are available to be controlled by the footswitch; and allow a user to drag and drop the object into one of the widgets having the icon, wherein dragging and dropping the object into one of the widgets displaying the icon causes the header module to do both of the following:

wirelessly pair with the footswitch, and assign the footswitch to the port corresponding to the widget.

11. The system of claim 10, wherein the footswitch comprises a single-pedal footswitch or a dual-pedal footswitch.

12. The system of claim 11, wherein the GUI is configured to display the icon only in widgets corresponding to ports controllable by a single pedal footswitch if the footswitch comprises a single-pedal footswitch, and wherein the GUI is configured to display the icon only in widgets corresponding to ports controllable by a dual-pedal footswitch if the footswitch comprises a dual-pedal footswitch.

13. The system of claim 11, wherein the GUI is configured to display a single-pedal footswitch icon in the object if the footswitch comprises a single-pedal footswitch, and wherein the GUI is configured to display a dual-pedal footswitch icon in the object if the footswitch comprises a dual-pedal footswitch.

14. The system of claim 10, wherein dragging and dropping the object into one of the widgets having the icon causes the GUI to display a footswitch icon in the widget.

15. The system of claim 10, wherein the footswitch is a first footswitch, wherein the object is a first object, wherein the system further comprises a second footswitch, and wherein the GUI is further configured to simultaneously display the first object and a second object indicating that the second footswitch is available to be assigned to one of the ports.

16. The system of claim 10, wherein the GUI is further configured to display a help balloon including instructions to drag and drop the object to assign the footswitch to one of the ports.

17. A method for assigning a footswitch to control a port of a modular energy system, wherein the modular energy system comprises an energy module and a display screen configured to render a graphical user interface, and wherein the energy module comprises ports configured to deliver energy modalities to surgical instruments coupled thereto, the method comprising:

displaying, by the GUI, a plurality of widgets corresponding to the ports;

detecting, by the modular energy system, that the footswitch is available to be assigned to one of the ports, wherein detecting, by the modular energy system, that the footswitch is available to be assigned to one of the ports comprises detecting that the footswitch is available to be wirelessly paired with the modular energy system;

displaying, by the GUI, an object indicating that the footswitch is available to be assigned to one of the ports based on the detection of the footswitch;

identifying, by the modular energy system, one or more of the ports that are available to be controlled by the footswitch;

displaying, by the GUI, an icon in the widgets corresponding to the one or more ports identified as available to be controlled by the footswitch, wherein the icon indicates that the port is available to be controlled by the footswitch;

assigning, by the modular energy system, the footswitch to one of the ports based on a user input, the user input including the user interacting with the GUI to drag and drop the object into one of the widgets having the icon indicating that the port is available to be controlled by the footswitch; and wirelessly pairing the footswitch with the modular energy system based on the user input such that the footswitch is both assigned to one of the ports and wirelessly paired with the modular energy system based on the same user input.

* * * * *